(12) United States Patent
Tapp et al.

(10) Patent No.: US 10,292,875 B2
(45) Date of Patent: May 21, 2019

(54) ABSORBENT ARTICLES WITH CHANNELS AND SIGNALS

(71) Applicant: The Procter & Gamble Company, Cincinnati, OH (US)

(72) Inventors: Ann Cecilia Tapp, West Chester, OH (US); Sarah Ann Sanborn, Frankfurt (DE); Rachael Eden Walther, Union, KY (US); Theodore Cory Fites, Cincinnati, OH (US); John Andrew Strasemeier, Aurora, IN (US)

(73) Assignee: The Procter & Gamble Company, Cincinnati, OH (US)

( * ) Notice: Subject to any disclaimer, the term of this patent is extended or adjusted under 35 U.S.C. 154(b) by 967 days.

(21) Appl. No.: 14/487,115

(22) Filed: Sep. 16, 2014

(65) Prior Publication Data

US 2015/0080839 A1 Mar. 19, 2015

Related U.S. Application Data

(60) Provisional application No. 61/878,297, filed on Sep. 16, 2013.

(51) Int. Cl.
*A61F 13/15* (2006.01)
*A61F 13/20* (2006.01)
(Continued)

(52) U.S. Cl.
CPC ...... *A61F 13/51394* (2013.01); *A61F 13/512* (2013.01); *A61F 13/535* (2013.01);
(Continued)

(58) Field of Classification Search
CPC .............. A61F 13/49001; A61F 13/533; A61F 2013/53754
See application file for complete search history.

(56) References Cited

U.S. PATENT DOCUMENTS

| 1,733,997 A | 10/1929 | Marr |
| 1,734,499 A | 11/1929 | Marinsky |

(Continued)

FOREIGN PATENT DOCUMENTS

| CA | 2001370 | 4/1990 |
| CA | 2291997 | 6/2000 |

(Continued)

OTHER PUBLICATIONS

American Chemical Society publication entitled "Contact Angle, Wettability and Adhesion", Advances in Chemistry Series 43, Chapter 7, edited by Robert F. Gould (Copyright 1964).

*Primary Examiner* — Michele M Kidwell
(74) *Attorney, Agent, or Firm* — Wednesday G. Shipp; Andrew J. Hagerty

(57) ABSTRACT

An absorbent article comprising a topsheet, a backsheet, an absorbent core comprising channels disposed between the topsheet and the backsheet, and a printed adhesive layer disposed between the topsheet and the absorbent core such that the printed adhesive layer is visible through the topsheet. At least a portion of the adhesive layer forms a pattern of one or more pairs of contoured lines that run lengthwise in the machine direction of the absorbent article, each pair being symmetric to its compliment across an axis of the absorbent article drawn in the machine direction and at the center of its width. The distance between the innermost pair of contoured lines is from about 15 mm to about 25 mm or the amount of adhesive comprising the printed adhesive layer is such that the pattern coverage with the adhesive is from about 15% to about 30%.

9 Claims, 7 Drawing Sheets

(51) Int. Cl.
  *A61F 13/513* (2006.01)
  *A61F 13/512* (2006.01)
  *A61F 13/535* (2006.01)
  *A61F 13/536* (2006.01)
  *A61F 13/537* (2006.01)
  *A61F 13/539* (2006.01)

(52) U.S. Cl.
  CPC ...... *A61F 13/536* (2013.01); *A61F 13/53747* (2013.01); *A61F 13/539* (2013.01)

(56) References Cited

U.S. PATENT DOCUMENTS

| | | |
|---|---|---|
| 1,989,283 A | 1/1935 | Limacher |
| 2,058,509 A | 10/1936 | Rose |
| 2,271,676 A | 2/1942 | Bjornbak |
| 2,450,789 A | 10/1948 | Frieman |
| 2,508,811 A | 5/1950 | Best et al. |
| 2,568,910 A | 9/1951 | Condylis |
| 2,570,796 A | 10/1951 | Gross |
| 2,570,963 A | 10/1951 | Mesmer |
| 2,583,553 A | 1/1952 | Faure |
| 2,705,957 A | 4/1955 | Mauro |
| 2,788,003 A | 4/1957 | Van Norden Morin |
| 2,788,786 A | 4/1957 | Dexter |
| 2,798,489 A | 7/1957 | Behrman |
| 2,807,263 A | 9/1957 | Newton |
| 2,830,589 A | 4/1958 | Doner |
| 2,890,700 A | 6/1959 | Lönberg-Holm |
| 2,890,701 A | 6/1959 | Weinman |
| 2,898,912 A | 8/1959 | Adams |
| 2,931,361 A | 4/1960 | Sostsrin |
| 2,977,957 A | 4/1961 | Clyne |
| 3,071,138 A | 1/1963 | Gustavo |
| 3,180,335 A | 4/1965 | Duncan et al. |
| 3,207,158 A | 9/1965 | Yoshitake et al. |
| 3,227,160 A | 1/1966 | Joy |
| 3,386,442 A | 6/1968 | Sabee |
| 3,561,446 A | 2/1971 | Jones |
| 3,572,342 A | 3/1971 | Lindquist et al. |
| 3,572,432 A | 3/1971 | Burton |
| 3,575,174 A | 4/1971 | Mogor |
| 3,578,155 A | 5/1971 | Small et al. |
| 3,606,887 A | 9/1971 | Roeder |
| 3,610,244 A | 10/1971 | Jones |
| 3,618,608 A | 11/1971 | Brink |
| 3,642,001 A | 2/1972 | Sabee |
| 3,653,381 A | 4/1972 | Warnken |
| 3,670,731 A | 6/1972 | Harmon |
| 3,688,767 A | 9/1972 | Goldstein |
| 3,710,797 A | 1/1973 | Marsan |
| 3,731,688 A | 5/1973 | Litt et al. |
| 3,756,878 A | 9/1973 | Willot |
| 3,774,241 A | 11/1973 | Zerkle |
| 3,776,233 A | 12/1973 | Schaar |
| 3,814,100 A | 6/1974 | Nystrand et al. |
| 3,828,784 A | 10/1974 | Sabee |
| 3,840,418 A | 10/1974 | Sabee |
| 3,847,702 A | 11/1974 | Jones |
| 3,848,594 A | 11/1974 | Buell |
| 3,848,595 A | 11/1974 | Endres |
| 3,848,597 A | 11/1974 | Endres |
| 3,860,003 A | 1/1975 | Buell |
| 3,863,637 A | 2/1975 | MacDonald et al. |
| 3,882,870 A | 5/1975 | Hathaway |
| 3,884,234 A | 5/1975 | Taylor |
| 3,900,032 A | 8/1975 | Heurlen |
| 3,911,173 A | 10/1975 | Sprague, Jr. |
| 3,920,017 A | 11/1975 | Karami |
| 3,924,626 A | 12/1975 | Lee et al. |
| 3,926,189 A | 12/1975 | Taylor |
| 3,929,134 A | 12/1975 | Karami |
| 3,929,135 A | 12/1975 | Thompson |
| 3,930,501 A | 1/1976 | Schaar |
| 3,938,523 A | 2/1976 | Gilliland et al. |
| 3,968,799 A | 7/1976 | Schrading |
| 3,978,861 A | 9/1976 | Schaar |
| 3,981,306 A | 9/1976 | Krusko |
| 3,987,794 A | 10/1976 | Schaar |
| 3,995,637 A | 12/1976 | Schaar |
| 3,995,640 A | 12/1976 | Schaar |
| 3,999,547 A | 12/1976 | Hernandez |
| 4,014,338 A | 3/1977 | Schaar |
| 4,034,760 A | 7/1977 | Amirsakis |
| 4,055,180 A | 10/1977 | Karami |
| 4,074,508 A | 2/1978 | Reid |
| 4,079,739 A | 3/1978 | Whitehead |
| 4,084,592 A | 4/1978 | Tritsch |
| 4,100,922 A | 7/1978 | Hernandez |
| 4,232,674 A | 11/1980 | Melican |
| 4,257,418 A | 3/1981 | Hessner |
| 4,259,220 A | 3/1981 | Bunnelle et al. |
| 4,296,750 A | 10/1981 | Woon et al. |
| 4,315,508 A | 2/1982 | Bolick |
| 4,324,246 A | 4/1982 | Mullane et al. |
| 4,340,706 A | 7/1982 | Obayashi et al. |
| 4,341,216 A | 7/1982 | Obenour |
| 4,342,314 A | 8/1982 | Radel et al. |
| 4,360,021 A | 11/1982 | Stima |
| 4,381,783 A | 5/1983 | Elias |
| 4,388,075 A | 6/1983 | Mesek et al. |
| 4,410,571 A | 10/1983 | Korpman |
| 4,461,621 A | 7/1984 | Karami et al. |
| 4,463,045 A | 7/1984 | Ahr et al. |
| 4,469,710 A | 9/1984 | Rielley et al. |
| 4,475,912 A | 10/1984 | Coates |
| 4,490,148 A | 12/1984 | Beckeström |
| 4,507,438 A | 3/1985 | Obayashi et al. |
| 4,515,595 A | 5/1985 | Kievet et al. |
| 4,527,990 A | 7/1985 | Sigl |
| 4,541,871 A | 9/1985 | Obayashi et al. |
| 4,551,191 A | 11/1985 | Kock et al. |
| 4,573,986 A | 3/1986 | Minetola et al. |
| 4,578,072 A | 3/1986 | Lancaster |
| 4,578,702 A | 3/1986 | Campbell |
| 4,585,448 A | 4/1986 | Enloe |
| 4,585,450 A | 4/1986 | Rosch et al. |
| 4,589,878 A | 5/1986 | Mitrani |
| 4,596,568 A | 6/1986 | Flug |
| 4,601,717 A | 7/1986 | Blevins |
| 4,606,964 A | 8/1986 | Wideman |
| 4,609,518 A | 9/1986 | Curro et al. |
| 4,610,678 A | 9/1986 | Weisman et al. |
| 4,623,342 A | 11/1986 | Ito et al. |
| 4,624,666 A | 11/1986 | Derossett |
| 4,629,643 A | 12/1986 | Curro et al. |
| 4,636,207 A | 1/1987 | Buell |
| 4,641,381 A | 2/1987 | Heran et al. |
| 4,646,510 A | 3/1987 | McIntyre |
| 4,662,875 A | 5/1987 | Hirotsu et al. |
| 4,666,983 A | 5/1987 | Tsubakimoto et al. |
| 4,670,011 A | 6/1987 | Mesek |
| 4,670,012 A | 6/1987 | Johnson |
| 4,680,030 A | 7/1987 | Coates et al. |
| 4,681,579 A | 7/1987 | Toussant et al. |
| 4,681,581 A | 7/1987 | Coates |
| 4,681,793 A | 7/1987 | Linman et al. |
| 4,690,680 A | 9/1987 | Higgins |
| 4,695,278 A | 9/1987 | Lawson |
| 4,699,622 A | 10/1987 | Toussant et al. |
| 4,704,115 A | 11/1987 | Buell |
| 4,704,116 A | 11/1987 | Enloe |
| 4,710,189 A | 12/1987 | Lash |
| 4,720,321 A | 1/1988 | Smith |
| 4,731,066 A | 3/1988 | Korpman |
| 4,731,070 A | 3/1988 | Koci |
| RE32,649 E | 4/1988 | Brandt et al. |
| 4,741,941 A | 5/1988 | Englebert et al. |
| 4,747,846 A | 5/1988 | Boland et al. |
| 4,753,648 A | 6/1988 | Jackson |
| 4,773,905 A | 9/1988 | Molee |
| 4,784,892 A | 11/1988 | Storey et al. |
| 4,785,996 A | 11/1988 | Ziecker et al. |
| 4,787,896 A | 11/1988 | Houghton et al. |

(56) References Cited

U.S. PATENT DOCUMENTS

| | | |
|---|---|---|
| 4,795,454 A | 1/1989 | Dragoo |
| 4,800,102 A | 1/1989 | Takada |
| 4,802,884 A | 2/1989 | Fröidh et al. |
| 4,806,408 A | 2/1989 | Pierre et al. |
| 4,806,598 A | 2/1989 | Morman |
| 4,808,176 A | 2/1989 | Kielpikowski |
| 4,808,178 A | 2/1989 | Aziz |
| 4,826,880 A | 5/1989 | Lesniak et al. |
| 4,834,735 A | 5/1989 | Alemany et al. |
| 4,834,740 A | 5/1989 | Suzuki et al. |
| 4,834,742 A | 5/1989 | Wilson et al. |
| 4,838,886 A | 6/1989 | Kent |
| 4,842,666 A | 6/1989 | Werenicz |
| 4,846,815 A | 7/1989 | Scripps |
| 4,846,825 A | 7/1989 | Enloe et al. |
| 4,848,815 A | 7/1989 | Molloy |
| 4,861,652 A | 8/1989 | Lippert et al. |
| 4,869,724 A | 9/1989 | Scripps |
| 4,886,697 A | 12/1989 | Perdelwitz, Jr. et al. |
| 4,888,231 A | 12/1989 | Angstadt |
| 4,892,528 A | 1/1990 | Suzuki et al. |
| 4,892,535 A | 1/1990 | Bjornberg |
| 4,892,536 A | 1/1990 | DesMarais et al. |
| 4,894,060 A | 1/1990 | Nestegard |
| 4,894,277 A | 1/1990 | Akasaki |
| 4,904,251 A | 2/1990 | Igaue et al. |
| 4,900,317 A | 3/1990 | Buell |
| 4,909,802 A | 3/1990 | Ahr et al. |
| 4,909,803 A | 3/1990 | Aziz et al. |
| 4,936,839 A | 6/1990 | Molee |
| 4,940,463 A | 7/1990 | Leathers et al. |
| 4,940,464 A | 7/1990 | Van Gompel et al. |
| 4,946,527 A | 8/1990 | Battrell |
| 4,950,264 A | 8/1990 | Osborn |
| 4,960,477 A | 10/1990 | Mesek |
| 4,963,140 A | 10/1990 | Robertson et al. |
| 4,966,809 A | 10/1990 | Tanaka et al. |
| 4,968,313 A | 11/1990 | Sabee |
| 4,990,147 A | 2/1991 | Freeland |
| 4,994,053 A | 2/1991 | Lang |
| 5,006,394 A | 4/1991 | Baird |
| 5,019,063 A | 5/1991 | Marsan et al. |
| 5,019,072 A | 5/1991 | Polski |
| 5,021,051 A | 6/1991 | Hiuke |
| 5,030,314 A | 7/1991 | Lang |
| 5,032,120 A | 7/1991 | Freeland et al. |
| 5,034,008 A | 7/1991 | Breitkopf |
| 5,037,416 A | 8/1991 | Allen et al. |
| 5,071,414 A | 8/1991 | Elliott |
| 5,072,687 A | 12/1991 | Mitchell |
| 5,085,654 A | 2/1992 | Buell |
| 5,087,255 A | 2/1992 | Sims et al. |
| 5,092,861 A | 3/1992 | Nomura et al. |
| 5,102,597 A | 4/1992 | Roe et al. |
| 5,114,420 A | 5/1992 | Igaue et al. |
| 5,124,188 A | 6/1992 | Roe et al. |
| 5,135,522 A | 8/1992 | Fahrenkrug et al. |
| 5,137,537 A | 8/1992 | Herron et al. |
| D329,697 S | 9/1992 | Fahrenkrug et al. |
| 5,143,679 A | 9/1992 | Weber et al. |
| 5,147,343 A | 9/1992 | Kellenberger |
| 5,147,345 A | 9/1992 | Young et al. |
| 5,149,334 A | 9/1992 | Roe et al. |
| 5,149,335 A | 9/1992 | Kellenberger et al. |
| 5,151,091 A | 9/1992 | Glaug |
| 5,151,092 A | 9/1992 | Buell et al. |
| 5,156,793 A | 10/1992 | Buell et al. |
| 5,167,653 A | 12/1992 | Igaue et al. |
| 5,167,897 A | 12/1992 | Weber et al. |
| 5,175,046 A | 12/1992 | Nguyen |
| 5,180,622 A | 1/1993 | Berg et al. |
| 5,190,563 A | 3/1993 | Herron et al. |
| 5,190,606 A | 3/1993 | Merkatoris et al. |
| 5,204,997 A | 4/1993 | Suzuki et al. |
| 5,213,817 A | 5/1993 | Pelley |
| 5,221,274 A | 6/1993 | Buell et al. |
| 5,235,515 A | 8/1993 | Ungpiyakul et al. |
| 5,242,436 A | 9/1993 | Weil et al. |
| 5,246,431 A | 9/1993 | Minetola et al. |
| 5,246,432 A | 9/1993 | Suzuki et al. |
| 5,246,433 A | 9/1993 | Hasse et al. |
| 5,248,309 A | 9/1993 | Serbiak et al. |
| 5,260,345 A | 11/1993 | Desmarais et al. |
| 5,269,775 A | 12/1993 | Freeland et al. |
| 5,281,683 A | 1/1994 | Yano et al. |
| H1298 H | 4/1994 | Ahr |
| 5,300,565 A | 4/1994 | Berg et al. |
| 5,312,386 A | 5/1994 | Correa et al. |
| 5,331,059 A | 7/1994 | Engelhardt et al. |
| 5,336,552 A | 8/1994 | Strack et al. |
| 5,348,547 A | 9/1994 | Payne et al. |
| 5,358,500 A | 10/1994 | LaVon et al. |
| 5,366,782 A | 11/1994 | Curro et al. |
| 5,382,610 A | 1/1995 | Harada et al. |
| 5,387,207 A | 2/1995 | Dyer et al. |
| 5,387,208 A | 2/1995 | Ashton et al. |
| 5,387,209 A | 2/1995 | Yamamoto et al. |
| 5,389,095 A | 2/1995 | Suzuki |
| 5,397,316 A | 3/1995 | Lavon et al. |
| 5,397,317 A | 3/1995 | Thomas |
| 5,399,175 A | 3/1995 | Glaug |
| 5,401,792 A | 3/1995 | Babu et al. |
| 5,409,771 A | 4/1995 | Dahmen et al. |
| H1440 H | 5/1995 | New et al. |
| 5,411,497 A | 5/1995 | Tanzer et al. |
| 5,415,644 A | 5/1995 | Enloe |
| 5,425,725 A | 6/1995 | Tanzer et al. |
| 5,429,630 A | 7/1995 | Beal et al. |
| 5,433,715 A | 7/1995 | Tanzer et al. |
| 5,451,219 A | 9/1995 | Suzuki |
| 5,451,442 A | 9/1995 | Pieniak |
| 5,460,622 A | 10/1995 | Dragoo et al. |
| 5,460,623 A | 10/1995 | Emenaker et al. |
| 5,462,541 A | 10/1995 | Bruemmer et al. |
| 5,476,458 A | 12/1995 | Glaug et al. |
| 5,486,166 A | 1/1996 | Bishop et al. |
| 5,486,167 A | 1/1996 | Dragoo et al. |
| 5,490,846 A | 2/1996 | Ellis et al. |
| 5,492,962 A | 2/1996 | Lahrman et al. |
| 5,494,622 A | 2/1996 | Heath et al. |
| 5,499,978 A | 3/1996 | Buell et al. |
| 5,507,736 A | 4/1996 | Clear et al. |
| 5,507,895 A | 4/1996 | Suekane |
| 5,509,915 A | 4/1996 | Hanson et al. |
| 5,514,104 A | 5/1996 | Cole |
| 5,518,801 A | 5/1996 | Chappell et al. |
| 5,520,674 A | 5/1996 | Hines et al. |
| 5,522,810 A | 6/1996 | Allen, Jr. |
| 5,527,300 A | 6/1996 | Sauer |
| 5,531,730 A | 7/1996 | Dreier |
| 5,532,323 A | 7/1996 | Yano et al. |
| 5,542,943 A | 8/1996 | Sageser |
| 5,549,592 A | 8/1996 | Fries et al. |
| 5,549,593 A | 8/1996 | Ygge et al. |
| 5,549,791 A | 8/1996 | Herron et al. |
| 5,554,145 A | 9/1996 | Roe et al. |
| 5,559,335 A | 9/1996 | Zing et al. |
| 5,560,878 A | 10/1996 | Dragoo et al. |
| 5,562,634 A | 10/1996 | Flumene et al. |
| 5,562,646 A | 10/1996 | Goldman et al. |
| 5,569,234 A | 10/1996 | Buell et al. |
| 5,571,096 A | 11/1996 | Dobrin et al. |
| 5,574,121 A | 11/1996 | Irie et al. |
| 5,575,783 A | 11/1996 | Clear et al. |
| 5,580,411 A | 12/1996 | Nease et al. |
| 5,584,829 A | 12/1996 | Lavash et al. |
| 5,586,979 A | 12/1996 | Thomas |
| 5,591,152 A | 1/1997 | Buell et al. |
| 5,591,155 A | 1/1997 | Nishikawa et al. |
| 5,593,399 A | 1/1997 | Tanzer et al. |
| 5,599,335 A | 2/1997 | Goldman et al. |
| 5,601,542 A | 2/1997 | Melius et al. |
| 5,607,414 A | 3/1997 | Richards et al. |
| 5,607,537 A | 3/1997 | Johnson et al. |

(56) References Cited

U.S. PATENT DOCUMENTS

| | | | |
|---|---|---|---|
| 5,607,760 A | 3/1997 | Roe | |
| 5,609,587 A | 3/1997 | Roe | |
| 5,609,588 A | 3/1997 | DiPalma et al. | |
| 5,611,879 A | 3/1997 | Morman | |
| 5,613,959 A | 3/1997 | Roessler et al. | |
| 5,613,960 A | 3/1997 | Mizutani | |
| 5,614,283 A | 3/1997 | Potnis et al. | |
| 5,622,589 A | 4/1997 | Johnson et al. | |
| 5,624,423 A | 4/1997 | Anjur | |
| 5,624,424 A | 4/1997 | Saisaka et al. | |
| 5,625,222 A | 4/1997 | Yoneda et al. | |
| 5,607,416 A | 5/1997 | Yamamoto et al. | |
| 5,626,571 A | 5/1997 | Young et al. | |
| 5,628,741 A | 5/1997 | Buell et al. | |
| 5,628,845 A | 5/1997 | Murray et al. | |
| 5,635,191 A | 6/1997 | Roe et al. | |
| 5,635,271 A | 6/1997 | Zafiroglu | |
| 5,637,106 A | 6/1997 | Mitchell | |
| 5,643,238 A | 7/1997 | Baker | |
| 5,643,243 A | 7/1997 | Klemp | |
| 5,643,588 A | 7/1997 | Roe et al. | |
| 5,649,914 A | 7/1997 | Glaug | |
| 5,650,214 A | 7/1997 | Anderson | |
| H1674 H | 8/1997 | Ames et al. | |
| 5,658,268 A | 8/1997 | Johns et al. | |
| 5,662,634 A | 9/1997 | Yamamoto et al. | |
| 5,662,638 A | 9/1997 | Johnson et al. | |
| 5,662,758 A | 9/1997 | Hamilton et al. | |
| 5,669,894 A | 9/1997 | Goldman et al. | |
| 5,674,215 A | 10/1997 | Ronnberg | |
| 5,681,300 A | 10/1997 | Ahr | |
| 5,683,374 A | 11/1997 | Yamamoto | |
| 5,683,752 A * | 11/1997 | Popp | A61F 13/15699 |
| | | | 118/668 |
| 5,685,874 A | 11/1997 | Buell et al. | |
| 5,690,624 A | 11/1997 | Sasaki et al. | |
| 5,690,627 A | 11/1997 | Clear et al. | |
| 5,691,035 A | 11/1997 | Chappell et al. | |
| 5,691,036 A | 11/1997 | Chappell et al. | |
| 5,695,488 A | 12/1997 | Sosalla | |
| 5,700,254 A | 12/1997 | McDowall et al. | |
| 5,702,376 A | 12/1997 | Glaug | |
| 5,714,156 A | 2/1998 | Schmidt et al. | |
| 5,723,087 A | 3/1998 | Chappell et al. | |
| 5,733,275 A | 3/1998 | Davis et al. | |
| 5,749,866 A | 5/1998 | Roe et al. | |
| 5,752,947 A | 5/1998 | Awolin | |
| 5,756,039 A | 5/1998 | Mcfall et al. | |
| H1732 H | 6/1998 | Johnson | |
| 5,762,641 A | 6/1998 | Bewick Sonntag et al. | |
| 5,766,388 A | 6/1998 | Pelley | |
| 5,766,389 A | 6/1998 | Brandon et al. | |
| 5,772,825 A | 6/1998 | Schmitz | |
| 5,776,121 A | 7/1998 | Roe et al. | |
| 5,779,831 A | 7/1998 | Schmitz | |
| 5,788,684 A | 8/1998 | Abuto et al. | |
| 5,795,345 A | 8/1998 | Mizutani | |
| 5,797,892 A | 8/1998 | Glaug | |
| 5,797,894 A | 8/1998 | Cadieux et al. | |
| 5,807,365 A | 9/1998 | Luceri | |
| 5,810,796 A | 9/1998 | Kimura et al. | |
| 5,810,800 A | 9/1998 | Hunter et al. | |
| 5,814,035 A | 9/1998 | Gryskiewicz et al. | |
| 5,820,618 A | 10/1998 | Roberts et al. | |
| 5,827,257 A | 10/1998 | Fujioka | |
| 5,830,202 A | 11/1998 | Bogdanski et al. | |
| 5,833,678 A | 11/1998 | Ashton et al. | |
| 5,837,789 A | 11/1998 | Stockhausen et al. | |
| 5,840,404 A | 11/1998 | Graff | |
| 5,843,059 A | 12/1998 | Niemeyer et al. | |
| 5,846,231 A | 12/1998 | Fujioka et al. | |
| 5,846,232 A | 12/1998 | Serbiak et al. | |
| 5,849,816 A | 12/1998 | Suskind et al. | |
| 5,851,204 A | 12/1998 | Mitzutani | |
| 5,855,572 A | 1/1999 | Schmidt | |
| 5,858,013 A | 1/1999 | Kling | |
| 5,858,515 A | 1/1999 | Stokes et al. | |
| 5,865,823 A | 2/1999 | Curro | |
| 5,865,824 A | 2/1999 | Chen | |
| 5,873,868 A | 2/1999 | Nakahata | |
| 5,876,391 A | 3/1999 | Roe et al. | |
| 5,879,751 A | 3/1999 | Bogdanski | |
| 5,891,118 A | 4/1999 | Toyoshima | |
| 5,891,544 A | 4/1999 | Chappell et al. | |
| 5,897,545 A | 4/1999 | Kline et al. | |
| 5,904,673 A | 5/1999 | Roe et al. | |
| 5,925,439 A | 7/1999 | Haubach | |
| 5,928,184 A | 7/1999 | Etheredge | |
| 5,931,825 A | 8/1999 | Kuen et al. | |
| 5,938,648 A | 8/1999 | Lavon et al. | |
| 5,938,650 A | 8/1999 | Baer et al. | |
| 5,941,862 A | 8/1999 | Haynes et al. | |
| 5,944,706 A | 8/1999 | Palumbo et al. | |
| 5,947,949 A | 9/1999 | Inoue et al. | |
| 5,951,536 A | 9/1999 | Osborn, III et al. | |
| 5,957,908 A | 9/1999 | Kline et al. | |
| 5,964,743 A * | 10/1999 | Abuto | A61F 13/5323 |
| | | | 604/385.01 |
| 5,968,025 A | 10/1999 | Roe et al. | |
| 5,968,029 A | 10/1999 | Chappell et al. | |
| 5,980,500 A | 11/1999 | Shimizu et al. | |
| 5,981,824 A | 11/1999 | Luceri | |
| 5,989,236 A | 11/1999 | Roe et al. | |
| 6,004,306 A | 12/1999 | Robles et al. | |
| 6,022,430 A | 2/2000 | Blenke et al. | |
| 6,022,431 A | 2/2000 | Blenke et al. | |
| 6,042,673 A | 3/2000 | Johnson et al. | |
| 6,050,984 A | 4/2000 | Fujioka | |
| 6,054,631 A | 4/2000 | Gent | |
| 6,056,732 A | 5/2000 | Fujioka et al. | |
| 6,060,115 A | 5/2000 | Borowski et al. | |
| 6,068,620 A | 5/2000 | Chmielewski | |
| 6,080,909 A | 6/2000 | Osterdahl et al. | |
| 6,083,210 A | 7/2000 | Young et al. | |
| 6,090,994 A | 7/2000 | Chen | |
| 6,091,336 A | 7/2000 | Zand | |
| 6,093,474 A | 7/2000 | Sironi | |
| 6,099,515 A | 8/2000 | Sugito | |
| 6,102,892 A | 8/2000 | Putzer et al. | |
| 6,103,814 A | 8/2000 | Van Drongelen et al. | |
| 6,107,537 A | 8/2000 | Elder et al. | |
| 6,110,157 A | 8/2000 | Schmidt | |
| 6,117,121 A | 9/2000 | Faulks et al. | |
| 6,117,803 A | 9/2000 | Morman et al. | |
| 6,120,486 A | 9/2000 | Toyoda et al. | |
| 6,120,487 A | 9/2000 | Ashton | |
| 6,120,489 A | 9/2000 | Johnson et al. | |
| 6,120,866 A | 9/2000 | Arakawa et al. | |
| 6,121,509 A | 9/2000 | Ashraf et al. | |
| 6,129,717 A | 10/2000 | Fujioka et al. | |
| 6,129,720 A | 10/2000 | Blenke et al. | |
| 6,132,411 A | 10/2000 | Huber et al. | |
| 6,139,912 A | 10/2000 | Onuschak | |
| 6,143,821 A | 11/2000 | Houben | |
| 6,152,908 A | 11/2000 | Widlund | |
| 6,156,023 A | 12/2000 | Yoshioka | |
| 6,156,424 A | 12/2000 | Taylor | |
| 6,160,197 A | 12/2000 | Lassen | |
| 6,165,160 A | 12/2000 | Suzuki et al. | |
| 6,174,302 B1 | 1/2001 | Kumasaka | |
| 6,177,606 B1 | 1/2001 | Etheredge | |
| 6,177,607 B1 | 1/2001 | Blaney et al. | |
| 6,186,996 B1 | 2/2001 | Martin | |
| 6,210,386 B1 | 4/2001 | Inoue | |
| 6,210,390 B1 | 4/2001 | Karlsson | |
| 6,231,556 B1 | 5/2001 | Osborn, III | |
| 6,231,557 B1 * | 5/2001 | Krautkramer | A61F 13/15203 |
| | | | 604/385.01 |
| 6,231,566 B1 | 5/2001 | Lai | |
| 6,238,380 B1 | 5/2001 | Sasaki | |
| 6,241,716 B1 | 6/2001 | Rönnberg | |
| 6,254,294 B1 | 7/2001 | Muhar | |
| 6,258,996 B1 | 7/2001 | Goldman | |
| 6,265,488 B1 | 7/2001 | Fujino et al. | |

(56) References Cited

U.S. PATENT DOCUMENTS

| | | |
|---|---|---|
| 6,290,686 B1 | 9/2001 | Tanzer et al. |
| 6,306,122 B1 | 10/2001 | Narawa et al. |
| 6,315,765 B1 | 11/2001 | Datta |
| 6,319,239 B1 | 11/2001 | Daniels et al. |
| 6,322,552 B1 | 11/2001 | Blenke et al. |
| 6,325,787 B1 | 12/2001 | Roe et al. |
| 6,326,525 B1 | 12/2001 | Hamajima |
| 6,330,735 B1 | 12/2001 | Hahn et al. |
| 6,334,858 B1 | 1/2002 | Rönnberg et al. |
| 6,336,922 B1 | 1/2002 | Van Gompel et al. |
| 6,340,611 B1 | 1/2002 | Shimizu |
| 6,342,715 B1 | 1/2002 | Shimizu |
| 6,402,731 B1 | 1/2002 | Suprise et al. |
| 6,350,332 B1 | 2/2002 | Thomas et al. |
| 6,368,687 B1 | 4/2002 | Joseph et al. |
| 6,371,948 B1 | 4/2002 | Mizutani |
| 6,372,952 B1 | 4/2002 | Lash et al. |
| 6,375,644 B2 | 4/2002 | Mizutani |
| 6,376,034 B1 | 4/2002 | Brander |
| 6,383,431 B1 | 5/2002 | Dobrin et al. |
| 6,383,960 B1 | 5/2002 | Everett et al. |
| 6,394,989 B2 | 5/2002 | Mizutani |
| 6,403,857 B1 | 6/2002 | Gross et al. |
| 6,406,467 B1 | 6/2002 | Dilnik et al. |
| 6,409,883 B1 | 6/2002 | Makolin |
| 6,410,820 B1 | 6/2002 | McFall et al. |
| 6,410,822 B1 | 6/2002 | Mizutani |
| 6,402,729 B1 | 7/2002 | Boberg et al. |
| 6,413,248 B1 | 7/2002 | Mizutani |
| 6,413,249 B1 | 7/2002 | Turi et al. |
| 6,414,214 B1 | 7/2002 | Engelhardt et al. |
| 6,416,502 B1 | 7/2002 | Connelly et al. |
| 6,416,697 B1 | 7/2002 | Venturino et al. |
| 6,419,667 B1 | 7/2002 | Avalon et al. |
| 6,423,046 B1 | 7/2002 | Fujioka et al. |
| 6,423,048 B1 | 7/2002 | Suzuki et al. |
| 6,423,884 B1 | 7/2002 | Oehmen |
| 6,429,350 B1 | 8/2002 | Tanzer et al. |
| 6,432,094 B1 | 8/2002 | Fujioka et al. |
| 6,432,098 B1 | 8/2002 | Kline et al. |
| 6,432,099 B2 | 8/2002 | Rönnberg |
| 6,437,214 B1 | 8/2002 | Everett et al. |
| 6,441,268 B1 | 8/2002 | Edwardsson |
| 6,443,933 B1 | 9/2002 | Suzuki et al. |
| 6,444,064 B1 | 9/2002 | Henry et al. |
| 6,447,496 B1 | 9/2002 | Mizutani |
| 6,458,111 B1 | 10/2002 | Onishi et al. |
| 6,458,877 B1 | 10/2002 | Ahmed et al. |
| 6,459,016 B1 | 10/2002 | Rosenfeld et al. |
| 6,461,034 B1 | 10/2002 | Schaefer et al. |
| 6,461,342 B2 | 10/2002 | Tanji et al. |
| 6,461,343 B1 | 10/2002 | Schaefer et al. |
| 6,472,478 B1 | 10/2002 | Daniel et al. |
| 6,475,201 B2 | 11/2002 | Saito et al. |
| 6,494,872 B1 | 12/2002 | Suzuki et al. |
| 6,494,873 B2 | 12/2002 | Karlsson et al. |
| 6,500,159 B1 | 12/2002 | Carvalho |
| 6,503,233 B1 | 1/2003 | Chen |
| 6,503,979 B1 | 1/2003 | Funk et al. |
| 6,506,186 B1 | 1/2003 | Roessler |
| 6,506,961 B1 | 1/2003 | Levy |
| 6,515,195 B1 | 2/2003 | Lariviere |
| 6,517,525 B1 | 2/2003 | Berthou |
| 6,518,479 B1 | 2/2003 | Graef |
| 6,520,947 B1 | 2/2003 | Tilly et al. |
| 6,521,811 B1 | 2/2003 | Lassen |
| 6,521,812 B1 | 2/2003 | Graef |
| 6,524,294 B1 | 2/2003 | Hilston et al. |
| 6,525,240 B1 | 2/2003 | Graef |
| 6,528,698 B2 | 3/2003 | Mizutani et al. |
| 6,529,860 B1 | 3/2003 | Strumolo et al. |
| 6,531,025 B1 | 3/2003 | Lender et al. |
| 6,531,027 B1 | 3/2003 | Lender et al. |
| 6,534,149 B1 | 3/2003 | Daley et al. |
| 6,559,081 B1 | 5/2003 | Erspamer |
| 6,559,239 B1 | 5/2003 | Riegel et al. |
| 6,562,168 B1 | 5/2003 | Schmitt et al. |
| 6,562,192 B1 | 5/2003 | Hamilton |
| 6,569,137 B2 | 5/2003 | Suzuki et al. |
| 6,573,422 B1 | 6/2003 | Rosenfeld |
| 6,585,713 B1 | 7/2003 | LaMahieu et al. |
| 6,585,858 B1 | 7/2003 | Otto et al. |
| 6,602,234 B2 | 8/2003 | Klemp et al. |
| 6,605,070 B2 | 8/2003 | Ludwig et al. |
| 6,605,172 B1 | 8/2003 | Anderson et al. |
| 6,605,752 B2 | 8/2003 | Magnusson et al. |
| 6,610,900 B1 | 8/2003 | Tanzer |
| 6,630,054 B1 | 10/2003 | Graef |
| 6,632,209 B1 | 10/2003 | Chmielewski |
| 6,632,504 B1 | 10/2003 | Gillespie et al. |
| 6,645,569 B2 | 11/2003 | Cramer et al. |
| 6,646,180 B1 | 11/2003 | Chmielewski |
| 6,648,869 B1 | 11/2003 | Gillies et al. |
| 6,648,870 B2 | 11/2003 | Itoh et al. |
| 6,648,871 B2 | 11/2003 | Kusibojoska et al. |
| 6,649,807 B2 | 11/2003 | Mizutani |
| 6,649,810 B1 | 11/2003 | Minato et al. |
| 6,657,015 B1 | 12/2003 | Daniel |
| 6,657,102 B2 | 12/2003 | Furuya |
| 6,667,424 B1 | 12/2003 | Hamilton |
| 6,670,522 B1 | 12/2003 | Graef |
| 6,673,982 B1 | 1/2004 | Chen |
| 6,673,983 B1 | 1/2004 | Graef |
| 6,673,985 B2 | 1/2004 | Mizutani |
| 6,682,515 B1 | 1/2004 | Mizutani et al. |
| 6,682,516 B2 | 1/2004 | Johnston |
| 6,689,115 B1 | 2/2004 | Popp et al. |
| 6,689,934 B2 | 2/2004 | Dodge, II et al. |
| 6,695,827 B2 | 2/2004 | Chen |
| 6,700,034 B1 | 3/2004 | Lindsay et al. |
| 6,703,538 B2 | 3/2004 | Lassen |
| 6,705,465 B2 | 3/2004 | Ling et al. |
| 6,706,129 B2 | 3/2004 | Ando et al. |
| 6,706,943 B2 | 3/2004 | Onishi |
| 6,710,224 B2 | 3/2004 | Chmielewski et al. |
| 6,710,225 B1 | 3/2004 | Everett et al. |
| 6,716,205 B2 | 4/2004 | Popp et al. |
| 6,716,441 B1 | 4/2004 | Roe et al. |
| 6,717,029 B2 | 4/2004 | Baker |
| 6,726,668 B2 | 4/2004 | Underhill et al. |
| 6,726,792 B1 | 4/2004 | Johnson et al. |
| 6,730,387 B2 | 5/2004 | Rezai et al. |
| 6,734,335 B1 | 5/2004 | Graef |
| 6,790,798 B1 | 9/2004 | Suzuki et al. |
| 6,802,834 B2 | 10/2004 | Melius et al. |
| 6,809,158 B2 | 10/2004 | Ikeuchi et al. |
| 6,811,642 B2 | 11/2004 | Ochi |
| 6,818,083 B2 | 11/2004 | Mcamish et al. |
| 6,818,166 B2 | 11/2004 | Edwardson et al. |
| 6,830,800 B2 | 12/2004 | Curro et al. |
| 6,832,905 B2 | 12/2004 | Delzer et al. |
| 6,840,929 B2 | 1/2005 | Kurata |
| 6,846,374 B2 | 1/2005 | Popp |
| 6,858,771 B2 | 2/2005 | Yoshimasa |
| 6,863,933 B2 | 3/2005 | Cramer et al. |
| 6,863,960 B2 | 3/2005 | Curro et al. |
| 6,867,345 B2 | 3/2005 | Shimoe et al. |
| 6,867,346 B1 | 3/2005 | Dopps |
| 6,878,433 B2 | 4/2005 | Curro et al. |
| 6,878,647 B1 | 4/2005 | Rezai |
| 6,880,211 B2 | 4/2005 | Jackson et al. |
| 6,891,080 B2 | 5/2005 | Minato |
| 6,904,865 B2 | 6/2005 | Klofta |
| 6,911,574 B1 | 6/2005 | Mizutani |
| 6,923,797 B2 | 8/2005 | Shinohara et al. |
| 6,923,926 B2 | 8/2005 | Walter et al. |
| 6,926,703 B2 | 8/2005 | Sugito |
| 6,929,629 B2 | 8/2005 | Drevik et al. |
| 6,939,914 B2 | 9/2005 | Qin et al. |
| 6,946,585 B2 | 9/2005 | Brown |
| 6,953,451 B2 | 10/2005 | Berba |
| 6,955,733 B2 | 10/2005 | Miller et al. |
| 6,962,578 B1 | 11/2005 | Lavon |
| 6,962,645 B2 | 11/2005 | Graef |

(56) References Cited

U.S. PATENT DOCUMENTS

| | | |
|---|---|---|
| 6,965,058 B1 | 11/2005 | Raidel |
| 6,969,781 B2 | 11/2005 | Graef |
| 6,972,010 B2 | 12/2005 | Pesce et al. |
| 6,972,011 B2 | 12/2005 | Maeda et al. |
| 6,979,564 B2 | 12/2005 | Glucksmann et al. |
| 6,982,052 B2 | 1/2006 | Daniels et al. |
| 7,001,167 B2 | 2/2006 | Venturino |
| 7,014,632 B2 | 3/2006 | Takino et al. |
| 7,015,370 B2 | 3/2006 | Watanabe |
| 7,037,299 B2 | 5/2006 | Turi et al. |
| 7,037,571 B2 | 5/2006 | Fish et al. |
| 7,048,726 B2 | 5/2006 | Kusagawa et al. |
| 7,056,311 B2 | 6/2006 | Kinoshita |
| 7,067,711 B2 | 6/2006 | Kinoshita et al. |
| 7,073,373 B2 | 7/2006 | La Fortune |
| 7,078,583 B2 | 7/2006 | Kudo |
| 7,090,665 B2 | 8/2006 | Ohashi |
| 7,108,759 B2 | 9/2006 | You |
| 7,108,916 B2 | 9/2006 | Ehrnsperger et al. |
| 7,112,621 B2 | 9/2006 | Rohrbaugh et al. |
| 7,122,713 B2 | 10/2006 | Komatsu |
| 7,125,470 B2 | 10/2006 | Graef |
| 7,132,585 B2 | 11/2006 | Kudo |
| 7,147,628 B2 | 12/2006 | Drevik |
| 7,150,729 B2 | 12/2006 | Shimada |
| 7,154,019 B2 | 12/2006 | Mishima et al. |
| 7,160,281 B2 | 1/2007 | Leminh et al. |
| 7,163,528 B2 | 1/2007 | Christon et al. |
| 7,166,190 B2 | 1/2007 | Graef |
| 7,169,136 B2 | 1/2007 | Otsubo |
| 7,183,360 B2 | 2/2007 | Daniel et al. |
| 7,189,888 B2 | 3/2007 | Wang et al. |
| 7,196,241 B2 | 3/2007 | Kinoshita |
| 7,199,211 B2 | 4/2007 | Popp et al. |
| 7,204,830 B2 | 4/2007 | Mishima |
| 7,207,978 B2 | 4/2007 | Takino |
| 7,219,403 B2 | 5/2007 | Miyamoto et al. |
| 7,220,251 B2 | 5/2007 | Otsubo et al. |
| 7,241,280 B2 | 7/2007 | Christen et al. |
| 7,250,481 B2 | 7/2007 | Jaworek et al. |
| 7,252,657 B2 | 8/2007 | Mishima |
| 7,265,258 B2 | 9/2007 | Hamilton |
| 7,270,651 B2 | 9/2007 | Adams et al. |
| 7,285,178 B2 | 10/2007 | Mischler et al. |
| RE39,919 E | 11/2007 | Dodge, II et al. |
| 7,306,582 B2 | 12/2007 | Adams et al. |
| 7,311,696 B2 | 12/2007 | Christen et al. |
| 7,311,968 B2 | 12/2007 | Ehrnsperger et al. |
| 7,312,372 B2 | 12/2007 | Miyama |
| 7,318,820 B2 | 1/2008 | LaVon et al. |
| 7,329,244 B2 | 2/2008 | Otsubo |
| 7,329,246 B2 | 2/2008 | Kinoshita |
| 7,335,810 B2 | 2/2008 | Yoshimasa et al. |
| 7,377,914 B2 | 5/2008 | LaVon |
| 7,402,157 B2 * | 7/2008 | Christon ............ A61F 13/15203 604/378 |
| 7,429,689 B2 | 9/2008 | Chen |
| 7,435,244 B2 | 10/2008 | Schroer et al. |
| 7,465,373 B2 | 12/2008 | Graef |
| 7,500,969 B2 | 3/2009 | Mishima |
| 7,504,552 B2 | 3/2009 | Tamura |
| 7,521,109 B2 | 4/2009 | Suzuki et al. |
| 7,521,587 B2 | 4/2009 | Busam et al. |
| 7,537,832 B2 | 5/2009 | Carlucci et al. |
| 7,547,815 B2 | 6/2009 | Ohashi |
| 7,550,646 B2 | 6/2009 | Tamura |
| 7,563,257 B2 | 7/2009 | Nakajima |
| 7,588,561 B2 | 9/2009 | Kenmochi |
| 7,594,904 B2 | 9/2009 | Rosenfeld |
| 7,598,428 B2 | 10/2009 | Gustavsson et al. |
| 7,625,363 B2 | 12/2009 | Yoshimasa |
| 7,641,642 B2 | 1/2010 | Murai et al. |
| 7,648,490 B2 | 1/2010 | Kuroda |
| 7,652,111 B2 | 1/2010 | Hermeling et al. |
| 7,666,173 B2 | 2/2010 | Mishima |
| 7,666,174 B2 | 2/2010 | Kawakami et al. |
| 7,686,790 B2 | 3/2010 | Rasmussen et al. |
| 7,687,596 B2 | 3/2010 | Hermeling et al. |
| 7,695,461 B2 | 4/2010 | Rosenfeld |
| 7,696,402 B2 | 4/2010 | Nishikawa |
| 7,708,725 B2 | 5/2010 | Tamagawa |
| 7,717,150 B2 | 5/2010 | Manabe |
| 7,718,844 B2 | 5/2010 | Olson |
| 7,722,587 B2 | 5/2010 | Suzuki et al. |
| 7,722,590 B2 | 5/2010 | Tsuji |
| 7,727,217 B2 | 6/2010 | Hancock-Cooke |
| 7,736,351 B2 | 6/2010 | Nigam |
| 7,737,324 B2 | 6/2010 | LaVon et al. |
| 7,744,576 B2 | 6/2010 | Busam et al. |
| 7,744,578 B2 | 6/2010 | Tanio et al. |
| 7,750,203 B2 | 7/2010 | Busam et al. |
| 7,754,822 B2 | 7/2010 | Daniel et al. |
| 7,754,940 B2 | 7/2010 | Brisebois |
| 7,759,540 B2 | 7/2010 | Litvay et al. |
| 7,763,004 B2 | 7/2010 | Beck |
| 7,767,875 B2 | 8/2010 | Olson |
| 7,767,876 B2 | 8/2010 | Davis et al. |
| 7,767,878 B2 | 8/2010 | Suzuki |
| 7,772,420 B2 | 8/2010 | Hermeling et al. |
| 7,786,341 B2 | 8/2010 | Schneider et al. |
| 7,795,492 B2 | 9/2010 | Vartiainen |
| 7,803,145 B2 | 9/2010 | Rosenfeld |
| 7,825,291 B2 | 11/2010 | Elfsberg et al. |
| 7,850,672 B2 | 12/2010 | Guidotti et al. |
| 7,851,667 B2 | 12/2010 | Becker et al. |
| 7,855,314 B2 | 12/2010 | Hanao |
| 7,857,797 B2 | 12/2010 | Kudo |
| 7,858,842 B2 | 12/2010 | Komatsu |
| 7,884,259 B2 | 2/2011 | Hanao |
| 7,888,549 B2 | 2/2011 | Jansson et al. |
| 7,910,797 B2 | 3/2011 | Nandrea |
| 7,931,636 B2 | 4/2011 | LaVon et al. |
| 7,935,207 B2 | 5/2011 | Zhao |
| 7,935,861 B2 | 5/2011 | Suzuki |
| 7,938,813 B2 | 5/2011 | Wang et al. |
| 7,942,858 B2 | 5/2011 | Francoeur |
| 7,951,126 B2 | 5/2011 | Nanjyo |
| 7,959,620 B2 | 6/2011 | Miura et al. |
| 7,982,091 B2 | 7/2011 | Konawa |
| 7,993,319 B2 | 8/2011 | Sperl |
| 8,017,827 B2 | 9/2011 | Hundorf et al. |
| 8,029,486 B2 | 10/2011 | Nakajima |
| 8,034,991 B2 | 10/2011 | Bruzadin et al. |
| 8,039,684 B2 | 10/2011 | Guidotti et al. |
| 8,052,454 B2 | 11/2011 | Polnyi |
| 8,057,620 B2 | 11/2011 | Perego et al. |
| 8,109,915 B2 | 2/2012 | Shimoe |
| 8,124,828 B2 | 2/2012 | Kline et al. |
| 8,133,212 B2 | 3/2012 | Takada |
| 8,148,598 B2 | 4/2012 | Tsang et al. |
| 8,163,124 B2 | 4/2012 | Moriura et al. |
| 8,167,862 B2 | 5/2012 | Digiacomantonio et al. |
| 8,173,858 B2 | 5/2012 | Kuroda |
| 8,178,747 B2 | 5/2012 | Venturino et al. |
| 8,183,430 B2 | 5/2012 | Hakansson et al. |
| 8,186,296 B2 | 5/2012 | Brown |
| 8,187,239 B2 | 5/2012 | LaVon et al. |
| 8,187,240 B2 | 5/2012 | Busam et al. |
| 8,198,506 B2 | 6/2012 | Venturino et al. |
| 8,211,815 B2 | 7/2012 | Baker |
| 8,236,715 B2 | 8/2012 | Schmidt et al. |
| 8,237,012 B2 | 8/2012 | Miyama |
| 8,246,594 B2 | 8/2012 | Sperl |
| 8,258,367 B2 | 9/2012 | Lawson et al. |
| 8,268,424 B1 | 9/2012 | Suzuki |
| 8,273,943 B2 | 9/2012 | Noda |
| 8,282,617 B2 | 10/2012 | Kaneda |
| 8,283,516 B2 | 10/2012 | Litvay |
| 8,317,766 B2 | 11/2012 | Naoto |
| 8,317,768 B2 | 11/2012 | Larsson |
| 8,319,005 B2 | 11/2012 | Becker et al. |
| 8,343,123 B2 | 1/2013 | Noda |
| 8,343,296 B2 | 1/2013 | Blessing et al. |
| 8,360,977 B2 | 1/2013 | Marttila |

(56) References Cited

U.S. PATENT DOCUMENTS

| | | | |
|---|---|---|---|
| 8,361,047 B2 | 1/2013 | Mukai | |
| 8,377,025 B2 | 2/2013 | Nakajima | |
| 8,388,590 B2 | 3/2013 | Mason et al. | |
| 8,450,555 B2 | 5/2013 | Nahn et al. | |
| 8,496,637 B2 | 7/2013 | Hundorf et al. | |
| 8,519,213 B2 | 8/2013 | Venturino et al. | |
| 8,524,355 B2 | 9/2013 | Nakaoka | |
| 8,552,252 B2 | 10/2013 | Hundorf et al. | |
| 8,568,566 B2 | 10/2013 | Jackels et al. | |
| 8,569,571 B2 | 10/2013 | Kline et al. | |
| 8,581,019 B2 | 11/2013 | Carlucci et al. | |
| 8,603,058 B2 | 12/2013 | Sprerl et al. | |
| 8,604,270 B2 | 12/2013 | Venturino et al. | |
| 8,633,347 B2 | 1/2014 | Bianco et al. | |
| 8,664,468 B2 | 3/2014 | Lawson et al. | |
| 8,674,170 B2 | 3/2014 | Busam et al. | |
| 8,734,417 B2 | 5/2014 | LaVon et al. | |
| 8,766,031 B2 | 7/2014 | Becker et al. | |
| 8,772,570 B2 | 7/2014 | Kawakami et al. | |
| 8,784,594 B2 | 7/2014 | Blessing et al. | |
| 8,785,715 B2 | 7/2014 | Wright et al. | |
| 8,791,318 B2 | 7/2014 | Becker et al. | |
| 8,936,584 B2 | 1/2015 | Zander et al. | |
| 9,056,034 B2 | 6/2015 | Akiyama | |
| 9,289,330 B2 | 3/2016 | Mason et al. | |
| 9,326,896 B2 | 5/2016 | Schaefer et al. | |
| 2001/0007065 A1 | 7/2001 | Blanchard | |
| 2001/0008964 A1 | 7/2001 | Kurata et al. | |
| 2001/0016548 A1 | 8/2001 | Kugler et al. | |
| 2001/0020157 A1 | 9/2001 | Mizutani | |
| 2001/0037101 A1 | 11/2001 | Allan et al. | |
| 2001/0044610 A1 | 11/2001 | Kim | |
| 2002/0007167 A1 | 1/2002 | Dan | |
| 2002/0007169 A1 | 1/2002 | Graef et al. | |
| 2002/0016122 A1 | 2/2002 | Curro et al. | |
| 2002/0016579 A1 | 2/2002 | Stenberg | |
| 2002/0045881 A1 | 4/2002 | Kusibojoska et al. | |
| 2002/0056516 A1 | 5/2002 | Ochi | |
| 2002/0058919 A1 | 5/2002 | Hamilton et al. | |
| 2002/0062112 A1 | 5/2002 | Mizutani | |
| 2002/0062115 A1 | 5/2002 | Wada et al. | |
| 2002/0062116 A1 | 5/2002 | Mizutani et al. | |
| 2002/0065498 A1 | 5/2002 | Ohashi | |
| 2002/0072471 A1 | 6/2002 | Ikeuchi et al. | |
| 2002/0082575 A1 | 6/2002 | Dan | |
| 2002/0087139 A1 | 7/2002 | Popp et al. | |
| 2002/0095127 A1 | 7/2002 | Fish et al. | |
| 2002/0102392 A1 | 8/2002 | Fish et al. | |
| 2002/0115969 A1 | 8/2002 | Maeda et al. | |
| 2002/0123728 A1 | 9/2002 | Graef et al. | |
| 2002/0123848 A1 | 9/2002 | Schneiderman et al. | |
| 2002/0151634 A1 | 10/2002 | Rohrbaugh et al. | |
| 2002/0151861 A1 | 10/2002 | Klemp et al. | |
| 2002/0173767 A1 | 11/2002 | Popp et al. | |
| 2002/0192366 A1 | 12/2002 | Cramer et al. | |
| 2002/0197695 A1 | 12/2002 | Glucksmann et al. | |
| 2003/0036741 A1 | 2/2003 | Abba et al. | |
| 2003/0078553 A1 | 4/2003 | Wada | |
| 2003/0084983 A1 | 5/2003 | Rangachari et al. | |
| 2003/0088223 A1 | 5/2003 | Vogt et al. | |
| 2003/0105190 A1 | 6/2003 | Diehl et al. | |
| 2003/0109839 A1 | 6/2003 | Costae et al. | |
| 2003/0114811 A1 | 6/2003 | Christen et al. | |
| 2003/0114816 A1 | 6/2003 | Underhill | |
| 2003/0114818 A1 | 6/2003 | Benecke et al. | |
| 2003/0115969 A1 | 6/2003 | Koyano et al. | |
| 2003/0120235 A1 | 6/2003 | Boulanger | |
| 2003/0120249 A1 | 6/2003 | Wulz et al. | |
| 2003/0135176 A1 | 7/2003 | Delzer et al. | |
| 2003/0135181 A1 | 7/2003 | Chen et al. | |
| 2003/0135182 A1 | 7/2003 | Woon et al. | |
| 2003/0139712 A1 | 7/2003 | Dodge | |
| 2003/0139715 A1 | 7/2003 | Dodge | |
| 2003/0139718 A1 | 7/2003 | Graef | |
| 2003/0144642 A1 | 7/2003 | Dopps | |
| 2003/0144644 A1 | 7/2003 | Murai et al. | |
| 2003/0148684 A1 | 8/2003 | Cramer et al. | |
| 2003/0148694 A1 | 8/2003 | Ghiam | |
| 2003/0158530 A1 | 8/2003 | Diehl et al. | |
| 2003/0158531 A1 | 8/2003 | Chmielewski | |
| 2003/0158532 A1 | 8/2003 | Magee et al. | |
| 2003/0167045 A1 | 9/2003 | Graef | |
| 2003/0171727 A1 | 9/2003 | Graef | |
| 2003/0208175 A1 | 11/2003 | Gross | |
| 2003/0225385 A1 | 12/2003 | Glaug | |
| 2003/0233082 A1 | 12/2003 | Kline et al. | |
| 2003/0236512 A1 | 12/2003 | Baker | |
| 2004/0019338 A1 | 1/2004 | Litvay et al. | |
| 2004/0022998 A1 | 2/2004 | Miyamoto et al. | |
| 2004/0033750 A1 | 2/2004 | Everett | |
| 2004/0063367 A1 | 4/2004 | Dodge | |
| 2004/0064113 A1 | 4/2004 | Erdman | |
| 2004/0064115 A1 | 4/2004 | Arora | |
| 2004/0064116 A1 | 4/2004 | Arora | |
| 2004/0064125 A1 | 4/2004 | Justmann et al. | |
| 2004/0065420 A1 | 4/2004 | Graef | |
| 2004/0082928 A1 | 4/2004 | Pesce et al. | |
| 2004/0097895 A1 | 5/2004 | Busam et al. | |
| 2004/0122411 A1 | 6/2004 | Hancock-Cooke | |
| 2004/0127131 A1 | 7/2004 | Potnis | |
| 2004/0127871 A1 | 7/2004 | Odorzynski | |
| 2004/0127872 A1 | 7/2004 | Petryk | |
| 2004/0134596 A1 | 7/2004 | Rosati et al. | |
| 2004/0138633 A1 | 7/2004 | Mishima et al. | |
| 2004/0147890 A1 | 7/2004 | Nakahata et al. | |
| 2004/0158212 A1 | 8/2004 | Ponomarenko et al. | |
| 2004/0162536 A1 | 8/2004 | Becker et al. | |
| 2004/0167486 A1 | 8/2004 | Busam et al. | |
| 2004/0167489 A1 | 8/2004 | Kellenberger et al. | |
| 2004/0170813 A1 | 9/2004 | Digiacomantonio et al. | |
| 2004/0193127 A1 | 9/2004 | Hansson | |
| 2004/0215160 A1 | 10/2004 | Chmielewski | |
| 2004/0220541 A1 | 11/2004 | Suzuki et al. | |
| 2004/0225271 A1 | 11/2004 | Datta et al. | |
| 2004/0231065 A1 | 11/2004 | Daniel et al. | |
| 2004/0236299 A1 | 11/2004 | Tsang et al. | |
| 2004/0236455 A1 | 11/2004 | Woltman et al. | |
| 2004/0249355 A1 | 12/2004 | Tanio et al. | |
| 2004/0260259 A1 | 12/2004 | Baker | |
| 2004/0265544 A1 | 12/2004 | DiSalvo et al. | |
| 2005/0001929 A1 | 1/2005 | Waksmundzki et al. | |
| 2005/0004543 A1 | 1/2005 | Schroer et al. | |
| 2005/0004548 A1 | 1/2005 | Otsubo et al. | |
| 2005/0008839 A1 | 1/2005 | Cramer et al. | |
| 2005/0018258 A1 | 1/2005 | Miyagi et al. | |
| 2005/0038401 A1 | 2/2005 | Suzuki et al. | |
| 2005/0070867 A1 | 3/2005 | Beruda et al. | |
| 2005/0085784 A1 | 4/2005 | LeMinh et al. | |
| 2005/0090789 A1 | 4/2005 | Graef | |
| 2005/0101929 A1 | 5/2005 | Waksmundzki et al. | |
| 2005/0137543 A1 | 6/2005 | Underhill et al. | |
| 2005/0148258 A1 | 7/2005 | Chakravarty | |
| 2005/0148961 A1 | 7/2005 | Sosalla et al. | |
| 2005/0148990 A1 | 7/2005 | Shimoe | |
| 2005/0154363 A1 | 7/2005 | Minato | |
| 2005/0159720 A1 | 7/2005 | Gentilcore | |
| 2005/0165208 A1 | 7/2005 | Popp et al. | |
| 2005/0171499 A1 | 8/2005 | Nigam et al. | |
| 2005/0176910 A1 | 8/2005 | Jaworek et al. | |
| 2005/0203475 A1 | 9/2005 | LaVon et al. | |
| 2005/0215752 A1 | 9/2005 | Popp et al. | |
| 2005/0217791 A1 | 10/2005 | Costello et al. | |
| 2005/0229543 A1 | 10/2005 | Tippey | |
| 2005/0234414 A1 | 10/2005 | Liu et al. | |
| 2005/0245684 A1 | 11/2005 | Daniel et al. | |
| 2005/0288645 A1 | 12/2005 | LaVon | |
| 2005/0288646 A1 | 12/2005 | LaVon | |
| 2006/0004333 A1* | 1/2006 | Olson | A61F 13/42 604/361 |
| 2006/0004334 A1 | 1/2006 | Schlinz et al. | |
| 2006/0021695 A1 | 2/2006 | Blessing et al. | |
| 2006/0024433 A1 | 2/2006 | Blessing et al. | |
| 2006/0069367 A1 | 3/2006 | Waksmundzki et al. | |
| 2006/0069371 A1 | 3/2006 | Ohashi et al. | |

(56) References Cited

U.S. PATENT DOCUMENTS

| | | |
|---|---|---|
| 2006/0073969 A1 | 4/2006 | Torli et al. |
| 2006/0081348 A1 | 4/2006 | Graef |
| 2006/0129114 A1 | 6/2006 | Mason et al. |
| 2006/0142724 A1 | 6/2006 | Watanabe et al. |
| 2006/0155057 A1 | 7/2006 | Hermeling et al. |
| 2006/0155254 A1 | 7/2006 | Sanz et al. |
| 2006/0167215 A1 | 7/2006 | Hermeling et al. |
| 2006/0177647 A1 | 8/2006 | Schmidt et al. |
| 2006/0178071 A1 | 8/2006 | Schmidt et al. |
| 2006/0184146 A1 | 8/2006 | Suzuki |
| 2006/0184149 A1 | 8/2006 | Kasai et al. |
| 2006/0189954 A1 | 8/2006 | Kudo |
| 2006/0202380 A1 | 9/2006 | Bentley |
| 2006/0206091 A1 | 9/2006 | Cole |
| 2006/0211828 A1 | 9/2006 | Daniel et al. |
| 2006/0240229 A1 | 10/2006 | Ehrnsperger et al. |
| 2006/0264860 A1 | 11/2006 | Beck |
| 2006/0264861 A1 | 11/2006 | Lavon et al. |
| 2006/0271010 A1 | 11/2006 | LaVon et al. |
| 2007/0027436 A1 | 2/2007 | Nakagawa et al. |
| 2007/0032770 A1 | 2/2007 | Lavon et al. |
| 2007/0043191 A1 | 2/2007 | Hermeling et al. |
| 2007/0043330 A1 | 2/2007 | Lankhof et al. |
| 2007/0044903 A1 | 3/2007 | Wisneski et al. |
| 2007/0049892 A1 | 3/2007 | Lord et al. |
| 2007/0049897 A1 | 3/2007 | LaVon et al. |
| 2007/0073253 A1 | 3/2007 | Miyama |
| 2007/0078422 A1 | 4/2007 | Glaug |
| 2007/0087169 A1* | 4/2007 | McFall ............ A61F 13/51496 428/172 |
| 2007/0088308 A1 | 4/2007 | Ehrnsperger et al. |
| 2007/0093164 A1 | 4/2007 | Nakaoka |
| 2007/0093767 A1 | 4/2007 | Carlucci et al. |
| 2007/0100307 A1 | 5/2007 | Nomoto |
| 2007/0118087 A1 | 5/2007 | Flohr et al. |
| 2007/0123834 A1 | 5/2007 | McDowall et al. |
| 2007/0156108 A1 | 7/2007 | Becker et al. |
| 2007/0156110 A1 | 7/2007 | Thyfault |
| 2007/0167928 A1 | 7/2007 | Becker et al. |
| 2007/0179464 A1 | 8/2007 | Becker et al. |
| 2007/0179469 A1 | 8/2007 | Takahashi et al. |
| 2007/0191798 A1 | 8/2007 | Glaug et al. |
| 2007/0219521 A1 | 9/2007 | Hird et al. |
| 2007/0219523 A1 | 9/2007 | Bruun |
| 2007/0244455 A1 | 10/2007 | Hansson et al. |
| 2007/0246147 A1 | 10/2007 | Venturino et al. |
| 2007/0255245 A1 | 11/2007 | Asp et al. |
| 2007/0282288 A1 | 12/2007 | Noda |
| 2007/0282290 A1 | 12/2007 | Cole |
| 2007/0282291 A1 | 12/2007 | Cole |
| 2008/0027402 A1 | 1/2008 | Schmidt et al. |
| 2008/0032035 A1 | 2/2008 | Schmidt et al. |
| 2008/0091159 A1 | 4/2008 | Carlucci et al. |
| 2008/0119810 A1 | 5/2008 | Kuroda |
| 2008/0125735 A1 | 5/2008 | Busam et al. |
| 2008/0132864 A1 | 6/2008 | Lawson et al. |
| 2008/0208154 A1 | 8/2008 | Oetjen et al. |
| 2008/0221538 A1 | 9/2008 | Zhao |
| 2008/0221539 A1 | 9/2008 | Zhao |
| 2008/0221543 A1* | 9/2008 | Wilkes ............. A61F 13/51496 604/385.01 |
| 2008/0228158 A1 | 9/2008 | Sue et al. |
| 2008/0262459 A1 | 10/2008 | Kamoto |
| 2008/0268194 A1 | 10/2008 | Kim et al. |
| 2008/0274227 A1 | 11/2008 | Boatman et al. |
| 2008/0281287 A1 | 11/2008 | Marcelo |
| 2008/0294139 A1* | 11/2008 | Ecker ................. A61F 13/4756 604/385.23 |
| 2008/0294140 A1 | 11/2008 | Ecker et al. |
| 2008/0312617 A1 | 12/2008 | Hundorf et al. |
| 2008/0312618 A1 | 12/2008 | Hundorf et al. |
| 2008/0312619 A1 | 12/2008 | Hundorf et al. |
| 2008/0312620 A1 | 12/2008 | Ashton et al. |
| 2008/0312621 A1 | 12/2008 | Hundorf et al. |
| 2008/0312622 A1 | 12/2008 | Hundorf et al. |
| 2008/0312623 A1 | 12/2008 | Hundorf et al. |
| 2008/0312624 A1 | 12/2008 | Hundorf et al. |
| 2008/0312625 A1 | 12/2008 | Hundorf et al. |
| 2008/0312627 A1 | 12/2008 | Takeuchi |
| 2008/0312628 A1 | 12/2008 | Hundorf et al. |
| 2009/0023848 A1 | 1/2009 | Ahmed et al. |
| 2009/0056867 A1 | 3/2009 | Moriura et al. |
| 2009/0062760 A1 | 3/2009 | Wright et al. |
| 2009/0112173 A1 | 4/2009 | Bissah |
| 2009/0112175 A1 | 4/2009 | Bissah et al. |
| 2009/0157022 A1 | 6/2009 | Macdonald |
| 2009/0192035 A1 | 7/2009 | Stueven et al. |
| 2009/0240220 A1 | 9/2009 | Macdonald |
| 2009/0058994 A1 | 10/2009 | Stueven et al. |
| 2009/0247977 A1 | 10/2009 | Takeuchi |
| 2009/0258994 A1 | 10/2009 | Stueven et al. |
| 2009/0270825 A1 | 10/2009 | Wciorka et al. |
| 2009/0298963 A1 | 12/2009 | Matsumoto et al. |
| 2009/0299312 A1 | 12/2009 | Macdonald |
| 2009/0306618 A1 | 12/2009 | Kudo |
| 2009/0318884 A1 | 12/2009 | Meyer et al. |
| 2009/0326494 A1 | 12/2009 | Uchida et al. |
| 2010/0051166 A1 | 3/2010 | Hundorf et al. |
| 2010/0062165 A1 | 3/2010 | Suzuki |
| 2010/0062934 A1 | 3/2010 | Suzuki |
| 2010/0063470 A1 | 3/2010 | Suzuki |
| 2010/0068520 A1 | 3/2010 | Stueven et al. |
| 2010/0082008 A1* | 4/2010 | Gagliardi ............ A61F 13/551 604/387 |
| 2010/0100065 A1 | 4/2010 | Bianco |
| 2010/0115237 A1 | 5/2010 | Brewer et al. |
| 2010/0121296 A1 | 5/2010 | Noda |
| 2010/0137773 A1 | 6/2010 | Gross |
| 2010/0137823 A1 | 6/2010 | Corneliusson |
| 2010/0198179 A1 | 8/2010 | Noda |
| 2010/0228210 A1 | 9/2010 | Busam et al. |
| 2010/0241096 A1 | 9/2010 | LaVon et al. |
| 2010/0241097 A1 | 9/2010 | Nigam et al. |
| 2010/0262099 A1 | 10/2010 | Klofta |
| 2010/0262104 A1 | 10/2010 | Carlucci et al. |
| 2010/0274208 A1 | 10/2010 | Gabrielii |
| 2010/0274210 A1 | 10/2010 | Noda |
| 2010/0312208 A1 | 12/2010 | Bond et al. |
| 2010/0324521 A1 | 12/2010 | Mukai |
| 2010/0324523 A1 | 12/2010 | Mukai |
| 2011/0041999 A1 | 2/2011 | Hundorf et al. |
| 2011/0060301 A1 | 3/2011 | Nishikawa et al. |
| 2011/0060303 A1 | 3/2011 | Bissah |
| 2011/0066127 A1 | 3/2011 | Kuwano |
| 2011/0071486 A1 | 3/2011 | Harada |
| 2011/0092944 A1 | 4/2011 | Sagisaka |
| 2011/0112498 A1 | 5/2011 | Nhan et al. |
| 2011/0125120 A1 | 5/2011 | Nishitani |
| 2011/0130732 A1 | 6/2011 | Jackels et al. |
| 2011/0130737 A1 | 6/2011 | Sagisaka |
| 2011/0137276 A1 | 6/2011 | Yoshikawa |
| 2011/0144602 A1 | 6/2011 | Long |
| 2011/0144604 A1 | 6/2011 | Noda |
| 2011/0144606 A1 | 6/2011 | Nandrea |
| 2011/0152813 A1 | 6/2011 | Ellingson |
| 2011/0166540 A1 | 7/2011 | Yang et al. |
| 2011/0172630 A1 | 7/2011 | Nomoto |
| 2011/0174430 A1 | 7/2011 | Zhao |
| 2011/0196330 A1 | 8/2011 | Hammons et al. |
| 2011/0208147 A1 | 8/2011 | Kawakami et al. |
| 2011/0250413 A1 | 10/2011 | Lu et al. |
| 2011/0268932 A1 | 11/2011 | Catalan et al. |
| 2011/0274834 A1 | 11/2011 | Brown et al. |
| 2011/0288513 A1 | 11/2011 | Hundorf et al. |
| 2011/0288514 A1 | 11/2011 | Kuroda |
| 2011/0295222 A1 | 12/2011 | Becker et al. |
| 2011/0319846 A1 | 12/2011 | Rinnert et al. |
| 2011/0319848 A1 | 12/2011 | McKiernan et al. |
| 2011/0319851 A1 | 12/2011 | Kudo |
| 2012/0004633 A1 | 1/2012 | Marcelo |
| 2012/0016326 A1 | 1/2012 | Brennan et al. |
| 2012/0022479 A1 | 1/2012 | Cotton |
| 2012/0029454 A1* | 2/2012 | Li ........................ A61F 13/49 604/367 |

(56) References Cited

U.S. PATENT DOCUMENTS

| | | |
|---|---|---|
| 2012/0035566 A1 | 2/2012 | Sagisaka |
| 2012/0035576 A1 | 2/2012 | Ichikawa |
| 2012/0064792 A1 | 3/2012 | Bauduin |
| 2012/0071848 A1 | 3/2012 | Zhang |
| 2012/0165771 A1 | 6/2012 | Ruman et al. |
| 2012/0165776 A1 | 6/2012 | Rinnert et al. |
| 2012/0175056 A1 | 7/2012 | Tsang |
| 2012/0184934 A1 | 7/2012 | Venturino |
| 2012/0232514 A1 | 9/2012 | Baker |
| 2012/0238977 A1 | 9/2012 | Oku |
| 2012/0253306 A1 | 10/2012 | Otsubo |
| 2012/0256750 A1 | 10/2012 | Novak |
| 2012/0271262 A1 | 10/2012 | Venturino |
| 2012/0170779 A1 | 12/2012 | Rosati et al. |
| 2012/0312491 A1 | 12/2012 | Jackels et al. |
| 2012/0316046 A1 | 12/2012 | Jackels et al. |
| 2012/0316523 A1 | 12/2012 | Hippe et al. |
| 2012/0316526 A1 | 12/2012 | Rosati et al. |
| 2012/0316527 A1 | 12/2012 | Rosati et al. |
| 2012/0316528 A1 | 12/2012 | Kreuzer et al. |
| 2012/0316529 A1 | 12/2012 | Kreuzer et al. |
| 2012/0323195 A1 | 12/2012 | Ehrnsperger et al. |
| 2012/0323201 A1 | 12/2012 | Bissah |
| 2012/0323202 A1 | 12/2012 | Bissah |
| 2013/0035656 A1 | 2/2013 | Moriya et al. |
| 2013/0041334 A1 | 2/2013 | Prioleau |
| 2013/0178811 A1 | 7/2013 | Kikuchi et al. |
| 2013/0211354 A1 | 8/2013 | Tsuji et al. |
| 2013/0211358 A1 | 8/2013 | Kikkawa et al. |
| 2013/0218115 A1 | 8/2013 | Katsuragawa et al. |
| 2013/0226119 A1 | 8/2013 | Katsuragawa et al. |
| 2013/0226120 A1 | 8/2013 | Van De Maele |
| 2013/0310784 A1 | 11/2013 | Bryant et al. |
| 2014/0005622 A1 | 1/2014 | Wirtz et al. |
| 2014/0005623 A1 | 1/2014 | Wirtz et al. |
| 2014/0027066 A1 | 1/2014 | Jackels et al. |
| 2014/0039437 A1 | 2/2014 | Van De Maele |
| 2014/0045683 A1 | 2/2014 | Loick et al. |
| 2014/0102183 A1 | 4/2014 | Agami et al. |
| 2014/0121623 A1 | 5/2014 | Kirby et al. |
| 2014/0135726 A1 | 5/2014 | Busam et al. |
| 2014/0142531 A1 | 5/2014 | Sasayama et al. |
| 2014/0163500 A1 | 6/2014 | Roe et al. |
| 2014/0163501 A1 | 6/2014 | Ehrnsperger et al. |
| 2014/0163502 A1 | 6/2014 | Arizti et al. |
| 2014/0163503 A1 | 6/2014 | Arizti et al. |
| 2014/0163506 A1 | 6/2014 | Roe et al. |
| 2014/0163511 A1 | 6/2014 | Roe et al. |
| 2014/0171893 A1 | 6/2014 | Lawson et al. |
| 2014/0318694 A1 | 10/2014 | Blessing et al. |
| 2014/0324007 A1 | 10/2014 | Hundorf et al. |
| 2014/0324008 A1 | 10/2014 | Hundorf et al. |
| 2015/0065981 A1 | 3/2015 | Roe et al. |
| 2015/0065986 A1 | 3/2015 | Blessing et al. |
| 2015/0080837 A1 | 3/2015 | Rosati et al. |
| 2015/0080839 A1 | 3/2015 | Tapp et al. |
| 2015/0173967 A1 | 6/2015 | Kreuzer et al. |
| 2015/0173968 A1 | 6/2015 | Joseph |
| 2015/0250662 A1 | 9/2015 | Isele et al. |
| 2016/0346136 A1* | 12/2016 | Strasemeier ............ A61F 13/42 |
| 2017/0020739 A1 | 1/2017 | Mason et al. |
| 2017/0020745 A1 | 1/2017 | Mason et al. |
| 2017/0081862 A1 | 3/2017 | Gu Bilmez |

FOREIGN PATENT DOCUMENTS

| | | |
|---|---|---|
| CA | 2308961 | 11/2000 |
| CA | 2487027 | 12/2003 |
| CA | 2561521 | 3/2007 |
| CA | 2630713 | 11/2008 |
| CA | 2636673 | 1/2009 |
| CA | 2712563 | 8/2010 |
| CA | 2702001 | 10/2010 |
| CN | 1238171 A | 12/1999 |
| CN | 2362468 Y | 2/2000 |
| CN | 1371671 | 2/2001 |
| CN | 2527254 Y | 12/2002 |
| CN | 2535020 Y | 2/2003 |
| CN | 2548609 Y | 5/2003 |
| CN | 1539391 | 10/2004 |
| CN | 1939242 | 4/2007 |
| CN | 101292930 | 10/2008 |
| CN | 201263750 | 7/2009 |
| CN | 201591689 | 9/2010 |
| CN | 201855366 U | 6/2011 |
| DE | 3205931 C2 | 9/1983 |
| DE | 3608114 A1 | 9/1987 |
| DE | 19732499 | 2/1999 |
| DE | 102 04 937 A1 | 8/2003 |
| EP | 083022 | 7/1983 |
| EP | 149880 | 7/1985 |
| EP | 0149880 A2 | 7/1985 |
| EP | 203289 | 12/1986 |
| EP | 0203289 A2 | 12/1986 |
| EP | 0206208 | 12/1986 |
| EP | 209561 B1 | 1/1987 |
| EP | 297411 B1 | 1/1989 |
| EP | 304957 | 3/1989 |
| EP | 374542 | 6/1990 |
| EP | 394274 | 10/1990 |
| EP | 0403832 | 12/1990 |
| EP | 481322 B1 | 4/1992 |
| EP | 530438 | 3/1993 |
| EP | 547847 | 6/1993 |
| EP | 555346 | 8/1993 |
| EP | 559476 | 9/1993 |
| EP | 591647 B2 | 4/1994 |
| EP | 597273 B1 | 5/1994 |
| EP | 601610 B2 | 6/1994 |
| EP | 632068 | 1/1995 |
| EP | 0640330 A1 | 3/1995 |
| EP | 0668066 | 9/1995 |
| EP | 685214 | 12/1995 |
| EP | 687453 | 12/1995 |
| EP | 0689817 | 1/1996 |
| EP | 0691133 | 1/1996 |
| EP | 0700673 | 3/1996 |
| EP | 0394274 | 7/1996 |
| EP | 724418 | 8/1996 |
| EP | 725613 | 8/1996 |
| EP | 725615 | 8/1996 |
| EP | 725616 | 8/1996 |
| EP | 758543 | 2/1997 |
| EP | 0761194 | 3/1997 |
| EP | 769284 | 4/1997 |
| EP | 0781537 | 7/1997 |
| EP | 783877 B1 | 7/1997 |
| EP | 787472 | 8/1997 |
| EP | 788874 B1 | 8/1997 |
| EP | 796068 | 9/1997 |
| EP | 799004 | 10/1997 |
| EP | 822794 B1 | 2/1998 |
| EP | 826351 | 3/1998 |
| EP | 844861 | 6/1998 |
| EP | 0737055 | 8/1998 |
| EP | 863733 | 9/1998 |
| EP | 971751 | 9/1998 |
| EP | 0875224 | 11/1998 |
| EP | 875224 A1 | 11/1998 |
| EP | 880955 | 12/1998 |
| EP | 891758 | 1/1999 |
| EP | 0893115 | 1/1999 |
| EP | 0724418 | 3/1999 |
| EP | 0725613 | 3/1999 |
| EP | 0725616 | 3/1999 |
| EP | 904755 | 3/1999 |
| EP | 0916327 | 5/1999 |
| EP | 925769 A2 | 6/1999 |
| EP | 933074 | 8/1999 |
| EP | 937736 | 8/1999 |
| EP | 941157 | 9/1999 |
| EP | 947549 | 10/1999 |
| EP | 951887 B1 | 10/1999 |
| EP | 0951890 | 10/1999 |

(56) References Cited

FOREIGN PATENT DOCUMENTS

| | | |
|---|---|---|
| EP | 2295493 | 10/1999 |
| EP | 2305749 | 10/1999 |
| EP | 2330152 | 10/1999 |
| EP | 953326 | 11/1999 |
| EP | 0978263 A1 | 2/2000 |
| EP | 985397 B1 | 3/2000 |
| EP | 0778762 | 4/2000 |
| EP | 1005847 | 6/2000 |
| EP | 1008333 | 6/2000 |
| EP | 1013252 B1 | 6/2000 |
| EP | 1018999 | 7/2000 |
| EP | 1019002 B1 | 7/2000 |
| EP | 1019003 B1 | 7/2000 |
| EP | 1022008 | 7/2000 |
| EP | 1023884 | 8/2000 |
| EP | 1053729 | 11/2000 |
| EP | 1059072 A2 | 12/2000 |
| EP | 1063954 | 1/2001 |
| EP | 1071388 | 1/2001 |
| EP | 1078618 | 2/2001 |
| EP | 1088537 A2 | 4/2001 |
| EP | 0796068 | 5/2001 |
| EP | 752892 | 7/2001 |
| EP | 1116479 A2 | 7/2001 |
| EP | 0790839 | 8/2001 |
| EP | 1132069 | 9/2001 |
| EP | 1173128 | 1/2002 |
| EP | 1175194 B1 | 1/2002 |
| EP | 1184018 | 3/2002 |
| EP | 1192312 B1 | 4/2002 |
| EP | 1196122 B2 | 4/2002 |
| EP | 1199059 | 4/2002 |
| EP | 1199327 | 4/2002 |
| EP | 1208824 | 5/2002 |
| EP | 0793469 | 6/2002 |
| EP | 1210925 | 6/2002 |
| EP | 1224922 | 7/2002 |
| EP | 1225857 | 7/2002 |
| EP | 1253231 | 10/2002 |
| EP | 1262531 A1 | 12/2002 |
| EP | 1263374 B1 | 12/2002 |
| EP | 0737056 | 1/2003 |
| EP | 1275358 | 1/2003 |
| EP | 1275361 | 1/2003 |
| EP | 1293187 | 3/2003 |
| EP | 1304986 B1 | 5/2003 |
| EP | 1332742 B1 | 8/2003 |
| EP | 1339368 | 9/2003 |
| EP | 1374817 | 1/2004 |
| EP | 1388334 | 2/2004 |
| EP | 1402863 | 3/2004 |
| EP | 962208 | 8/2004 |
| EP | 1447066 | 8/2004 |
| EP | 1447067 | 8/2004 |
| EP | 1460987 | 9/2004 |
| EP | 963749 | 11/2004 |
| EP | 1495739 | 1/2005 |
| EP | 1524955 | 4/2005 |
| EP | 1920743 | 4/2005 |
| EP | 1541103 | 6/2005 |
| EP | 1551344 | 7/2005 |
| EP | 1586289 | 10/2005 |
| EP | 1588723 | 10/2005 |
| EP | 1605882 | 12/2005 |
| EP | 1609448 | 12/2005 |
| EP | 1621166 | 2/2006 |
| EP | 1621167 | 2/2006 |
| EP | 1632206 | 3/2006 |
| EP | 1642556 | 4/2006 |
| EP | 1403419 | 5/2006 |
| EP | 1656162 | 5/2006 |
| EP | 1669046 | 6/2006 |
| EP | 1688114 | 8/2006 |
| EP | 2314265 | 8/2006 |
| EP | 1723939 | 11/2006 |
| EP | 1738727 | 1/2007 |
| EP | 1754461 | 2/2007 |
| EP | 1787611 | 5/2007 |
| EP | 1813238 | 8/2007 |
| EP | 2008626 | 12/2008 |
| EP | 2055279 A1 | 5/2009 |
| EP | 2093049 | 8/2009 |
| EP | 2130522 | 12/2009 |
| EP | 1621165 | 4/2010 |
| EP | 2444046 | 4/2012 |
| EP | 2532328 | 12/2012 |
| EP | 2532329 A1 | 12/2012 |
| EP | 2532332 A1 | 12/2012 |
| EP | 2679210 A1 | 1/2014 |
| EP | 2740449 | 6/2014 |
| EP | 2740450 | 6/2014 |
| EP | 2740452 | 6/2014 |
| ES | 2213491 | 8/2004 |
| FR | 2566631 | 1/1986 |
| FR | 2583377 | 12/1986 |
| FR | 2612770 | 9/1988 |
| FR | 2810234 | 12/2001 |
| GB | 1333081 A | 8/1971 |
| GB | 1307441 | 2/1973 |
| GB | 1513055 | 6/1978 |
| GB | 2101468 | 1/1983 |
| GB | 2170108 | 7/1986 |
| GB | 2262873 | 7/1993 |
| GB | 2288540 A | 6/1994 |
| GB | 2354449 | 3/2001 |
| GB | 2452260 A | 10/2007 |
| GR | 851769 | 11/1985 |
| IN | 0984/KOL/1999 | 10/2005 |
| IN | 212479 B | 3/2007 |
| IN | 208543 B | 8/2007 |
| IN | 0980/MUM/2009 | 6/2009 |
| JP | 5572928 U | 5/1980 |
| JP | 598322 U | 1/1984 |
| JP | 630148323 U | 9/1988 |
| JP | 2107250 | 4/1990 |
| JP | 03224481 B2 | 10/1991 |
| JP | 04122256 | 4/1992 |
| JP | 04341368 | 11/1992 |
| JP | 06191505 | 7/1994 |
| JP | 06269475 A | 9/1994 |
| JP | 07124193 | 5/1995 |
| JP | 08215629 | 8/1996 |
| JP | H10295728 | 11/1998 |
| JP | 10328232 | 12/1998 |
| JP | 11033056 A | 2/1999 |
| JP | 11318980 | 11/1999 |
| JP | 11320742 | 11/1999 |
| JP | 2000232985 | 8/2000 |
| JP | 2000238161 | 9/2000 |
| JP | 2001037810 | 2/2001 |
| JP | 2001046435 A | 2/2001 |
| JP | 2001120597 | 5/2001 |
| JP | 2001158074 | 6/2001 |
| JP | 2001178768 A | 7/2001 |
| JP | 2001198157 | 7/2001 |
| JP | 2001224626 A | 8/2001 |
| JP | 2001277394 | 10/2001 |
| JP | 03420481 B2 | 11/2001 |
| JP | 2001321397 | 11/2001 |
| JP | 2001353174 A | 12/2001 |
| JP | 2002052042 A | 2/2002 |
| JP | 2002065718 | 3/2002 |
| JP | 2002113800 A | 4/2002 |
| JP | 2002165832 | 6/2002 |
| JP | 2002165836 | 6/2002 |
| JP | 2002178429 | 6/2002 |
| JP | 2002272769 A | 9/2002 |
| JP | 2002320641 | 11/2002 |
| JP | 2002325792 A | 11/2002 |
| JP | 2002325799 A | 11/2002 |
| JP | 2002369841 A | 12/2002 |
| JP | 2003126140 | 5/2003 |
| JP | 2003153955 A | 5/2003 |
| JP | 2003265523 | 9/2003 |

(56) References Cited

FOREIGN PATENT DOCUMENTS

| | | |
|---|---|---|
| JP | 2003265524 A | 9/2003 |
| JP | 2003275237 | 9/2003 |
| JP | 2003325563 | 11/2003 |
| JP | 2004089269 | 3/2004 |
| JP | 03566012 B2 | 6/2004 |
| JP | 03568146 B2 | 6/2004 |
| JP | 03616077 B2 | 11/2004 |
| JP | 2004337314 A | 12/2004 |
| JP | 2004337385 A | 12/2004 |
| JP | 2004350864 | 12/2004 |
| JP | 03640475 B2 | 1/2005 |
| JP | 2005000312 A | 1/2005 |
| JP | 03660816 B2 | 3/2005 |
| JP | 03676219 B2 | 5/2005 |
| JP | 03688403 B2 | 6/2005 |
| JP | 03705943 B2 | 8/2005 |
| JP | 03719819 B2 | 9/2005 |
| JP | 03724963 B2 | 9/2005 |
| JP | 03725008 B2 | 9/2005 |
| JP | 03737376 B2 | 11/2005 |
| JP | 2006014792 A | 1/2006 |
| JP | 03781617 B2 | 3/2006 |
| JP | 2006110329 | 4/2006 |
| JP | 2006513824 T | 4/2006 |
| JP | 03801449 B2 | 5/2006 |
| JP | 2006116036 A | 5/2006 |
| JP | 03850102 B2 | 9/2006 |
| JP | 03850207 B2 | 9/2006 |
| JP | 03856941 B2 | 9/2006 |
| JP | 03868628 B2 | 10/2006 |
| JP | 03874499 B2 | 11/2006 |
| JP | 03877702 B2 | 11/2006 |
| JP | 2006325639 A | 12/2006 |
| JP | 2006346021 | 12/2006 |
| JP | 03904356 B2 | 1/2007 |
| JP | 2007007455 A | 1/2007 |
| JP | 2007007456 A | 1/2007 |
| JP | 03926042 B2 | 3/2007 |
| JP | 03934855 B2 | 3/2007 |
| JP | 2007089906 A | 4/2007 |
| JP | 2007105198 A | 4/2007 |
| JP | 2007152033 A | 6/2007 |
| JP | 03986210 B2 | 7/2007 |
| JP | 03986222 B2 | 7/2007 |
| JP | 2007167453 | 7/2007 |
| JP | 2007175515 A | 7/2007 |
| JP | 2007195665 A | 8/2007 |
| JP | 2007267763 A | 10/2007 |
| JP | 2007275491 A | 10/2007 |
| JP | 04035341 B2 | 11/2007 |
| JP | 04058281 B2 | 12/2007 |
| JP | 04061086 B2 | 12/2007 |
| JP | 04092319 B2 | 3/2008 |
| JP | 2008080150 A | 4/2008 |
| JP | 2008093289 A | 4/2008 |
| JP | 04124322 B2 | 5/2008 |
| JP | 2008119081 A | 5/2008 |
| JP | 2008136739 A | 6/2008 |
| JP | 2008136877 A | 6/2008 |
| JP | 04148594 B2 | 7/2008 |
| JP | 04148620 B2 | 7/2008 |
| JP | 2008154606 A | 7/2008 |
| JP | 04162609 B2 | 8/2008 |
| JP | 04162637 B2 | 8/2008 |
| JP | 04166923 B2 | 8/2008 |
| JP | 04167406 B2 | 8/2008 |
| JP | 04173723 B2 | 8/2008 |
| JP | 04190675 B2 | 9/2008 |
| JP | 04190693 B2 | 9/2008 |
| JP | 04208338 B2 | 10/2008 |
| JP | 2008246089 | 10/2008 |
| JP | 4177770 B2 | 11/2008 |
| JP | 04230971 B2 | 12/2008 |
| JP | 2008295475 A | 12/2008 |
| JP | 2008295713 A | 12/2008 |
| JP | 04261593 B2 | 2/2009 |
| JP | 2009112590 | 5/2009 |
| JP | 04322228 B2 | 6/2009 |
| JP | 2009136601 | 6/2009 |
| JP | 2009142401 A | 7/2009 |
| JP | 2009201878 A | 9/2009 |
| JP | 04392936 B2 | 10/2009 |
| JP | 2009232987 A | 10/2009 |
| JP | 2009261777 A | 11/2009 |
| JP | 2009291473 A | 12/2009 |
| JP | 2009297048 A | 12/2009 |
| JP | 2010017342 | 1/2010 |
| JP | 04458702 B2 | 2/2010 |
| JP | 04459013 B2 | 2/2010 |
| JP | 2010022560 | 2/2010 |
| JP | 04481325 B2 | 3/2010 |
| JP | 2010051654 A | 3/2010 |
| JP | 2010063814 A | 3/2010 |
| JP | 2010063944 A | 3/2010 |
| JP | 04492957 B2 | 4/2010 |
| JP | 2010068954 A | 4/2010 |
| JP | 2010075462 A | 4/2010 |
| JP | 2010082059 A | 4/2010 |
| JP | 2010104545 A | 5/2010 |
| JP | 2010104547 A | 5/2010 |
| JP | 2010110535 A | 5/2010 |
| JP | 2010119454 A | 6/2010 |
| JP | 2010119605 A | 6/2010 |
| JP | 2010119743 A | 6/2010 |
| JP | 2010131131 A | 6/2010 |
| JP | 2010131132 A | 6/2010 |
| JP | 2010131206 | 6/2010 |
| JP | 2010131297 A | 6/2010 |
| JP | 2010136917 A | 6/2010 |
| JP | 2010136973 A | 6/2010 |
| JP | 04540563 B2 | 7/2010 |
| JP | 04587947 B2 | 9/2010 |
| JP | 2010194124 A | 9/2010 |
| JP | 2010201093 | 9/2010 |
| JP | 2010221067 | 10/2010 |
| JP | 4577766 B2 | 11/2010 |
| JP | 04620299 B2 | 11/2010 |
| JP | 04627472 B2 | 11/2010 |
| JP | 04627473 B2 | 11/2010 |
| JP | 04638087 B2 | 12/2010 |
| JP | 04652626 B2 | 12/2010 |
| JP | 2010273842 A | 12/2010 |
| JP | 2010284418 A | 12/2010 |
| JP | 2011000480 A | 1/2011 |
| JP | 2011030700 | 2/2011 |
| JP | 04693574 B2 | 3/2011 |
| JP | 2011067484 A | 4/2011 |
| JP | 2011072720 A | 4/2011 |
| JP | 2011104014 | 6/2011 |
| JP | 2011104122 A | 6/2011 |
| JP | 2011120661 A | 6/2011 |
| JP | 2011125360 A | 6/2011 |
| JP | 2011125537 | 6/2011 |
| JP | 04776516 B2 | 7/2011 |
| JP | 2011130797 A | 7/2011 |
| JP | 2011130799 A | 7/2011 |
| JP | 2011156032 A | 8/2011 |
| JP | 2011156070 A | 8/2011 |
| JP | 2011156254 | 8/2011 |
| JP | 04824882 B2 | 9/2011 |
| JP | 4850272 B2 | 10/2011 |
| JP | 04855533 B2 | 11/2011 |
| JP | 2011239858 | 12/2011 |
| JP | 04931572 B2 | 2/2012 |
| JP | 04937225 B2 | 3/2012 |
| JP | 04953618 B2 | 3/2012 |
| JP | 04969437 B2 | 4/2012 |
| JP | 04969640 B2 | 4/2012 |
| JP | 4971491 B2 | 4/2012 |
| JP | 04974524 B2 | 4/2012 |
| JP | 04979780 B2 | 4/2012 |
| JP | 05016020 B2 | 6/2012 |
| JP | 05027364 B2 | 6/2012 |
| JP | 2012115378 | 6/2012 |

(56) References Cited

FOREIGN PATENT DOCUMENTS

| | | |
|---|---|---|
| JP | 05031082 B2 | 7/2012 |
| JP | 05042351 B2 | 7/2012 |
| JP | 05043569 B2 | 7/2012 |
| JP | 05043591 B2 | 7/2012 |
| JP | 05046488 B2 | 7/2012 |
| JP | 2012125452 | 7/2012 |
| JP | 2012125625 A | 7/2012 |
| JP | 05053765 B2 | 8/2012 |
| JP | 05070275 B2 | 8/2012 |
| JP | 05079931 B1 | 9/2012 |
| JP | 05080189 B2 | 9/2012 |
| JP | 05084442 B2 | 9/2012 |
| JP | 05084476 B2 | 9/2012 |
| JP | 5085770 B2 | 9/2012 |
| JP | 05089269 B2 | 9/2012 |
| JP | 2012179286 | 9/2012 |
| JP | 05113146 B2 | 10/2012 |
| JP | 05129536 B2 | 11/2012 |
| JP | 05105884 B2 | 12/2012 |
| JP | 5715806 B2 | 5/2015 |
| KR | 20010005620 | 1/2001 |
| KR | 20020035634 | 5/2002 |
| KR | 20080028771 | 4/2008 |
| SE | 9400916 | 3/1994 |
| SE | 9704893 | 12/1997 |
| WO | WO 90/15830 | 12/1990 |
| WO | WO9219198 | 11/1992 |
| WO | WO 93/21237 | 10/1993 |
| WO | WO9321879 | 11/1993 |
| WO | WO9510996 | 4/1995 |
| WO | WO9511652 | 5/1995 |
| WO | WO9514453 | 6/1995 |
| WO | WO9515139 | 6/1995 |
| WO | WO9516424 | 6/1995 |
| WO | WO9516746 | 6/1995 |
| WO | WO9519753 | 7/1995 |
| WO | WO9521596 | 8/1995 |
| WO | WO9524173 | 9/1995 |
| WO | WO9526209 | 10/1995 |
| WO | WO9529657 | 11/1995 |
| WO | WO9532698 | 12/1995 |
| WO | WO9534329 | 12/1995 |
| WO | WO9616624 | 6/1996 |
| WO | WO9619173 | 6/1996 |
| WO | WO96029967 | 10/1996 |
| WO | WO9711659 | 4/1997 |
| WO | WO9717922 | 5/1997 |
| WO | WO 9724096 | 7/1997 |
| WO | WO9816179 | 4/1998 |
| WO | WO9816180 | 4/1998 |
| WO | WO9843684 | 10/1998 |
| WO | WO9913813 | 3/1999 |
| WO | WO9934841 | 7/1999 |
| WO | WO9951178 | 10/1999 |
| WO | WO200000235 | 1/2000 |
| WO | WO200032145 | 6/2000 |
| WO | WO200059430 | 10/2000 |
| WO | WO200115647 | 3/2001 |
| WO | WO200126596 | 4/2001 |
| WO | WO 0135886 | 5/2001 |
| WO | WO200207663 | 1/2002 |
| WO | WO200232962 | 4/2002 |
| WO | WO2002064877 | 8/2002 |
| WO | WO2002067809 | 9/2002 |
| WO | WO2003009794 | 2/2003 |
| WO | WO2003039402 | 5/2003 |
| WO | WO2003053297 | 7/2003 |
| WO | WO03079946 | 10/2003 |
| WO | WO03101622 | 12/2003 |
| WO | WO2003105738 | 12/2003 |
| WO | WO2004021946 | 3/2004 |
| WO | WO2004049995 | 6/2004 |
| WO | WO2004071539 | 8/2004 |
| WO | WO2004084784 | 10/2004 |
| WO | WO2004105664 | 12/2004 |
| WO | WO2005/018694 | 3/2005 |
| WO | WO2005087164 | 9/2005 |
| WO | WO 2005/102237 | 11/2005 |
| WO | WO2006104024 | 5/2006 |
| WO | WO2006059922 | 6/2006 |
| WO | WO2006062258 | 6/2006 |
| WO | WO2006066029 | 6/2006 |
| WO | WO2006083584 | 8/2006 |
| WO | WO2006134904 | 12/2006 |
| WO | WO2006134906 | 12/2006 |
| WO | WO2007000315 | 1/2007 |
| WO | WO2007046052 | 4/2007 |
| WO | WO2007047598 | 4/2007 |
| WO | WO2007049725 | 5/2007 |
| WO | WO2007061035 | 5/2007 |
| WO | WO 2007/141744 | 12/2007 |
| WO | WO2007142145 | 12/2007 |
| WO | WO2007148502 | 12/2007 |
| WO | WO2008018922 | 2/2008 |
| WO | WO2008065945 | 6/2008 |
| WO | WO2008146749 | 12/2008 |
| WO | WO2008155699 | 12/2008 |
| WO | WO2009004941 | 1/2009 |
| WO | WO2009005431 | 1/2009 |
| WO | WO2009139248 | 1/2009 |
| WO | WO2009139255 | 1/2009 |
| WO | WO2009041223 | 4/2009 |
| WO | WO2009096108 | 8/2009 |
| WO | WO2009107435 | 9/2009 |
| WO | WO2009122830 | 10/2009 |
| WO | WO 2009/155265 | 12/2009 |
| WO | WO2009152018 | 12/2009 |
| WO | WO2009155264 | 12/2009 |
| WO | WO2009155265 | 12/2009 |
| WO | WO2010071508 | 6/2010 |
| WO | WO2010074319 | 7/2010 |
| WO | WO2010107096 | 9/2010 |
| WO | WO2010114052 | 10/2010 |
| WO | WO2010117015 | 10/2010 |
| WO | WO2010118272 | 10/2010 |
| WO | WO201153044 | 5/2011 |
| WO | WO2011118725 | 9/2011 |
| WO | WO2011118842 | 9/2011 |
| WO | WO2011145653 | 11/2011 |
| WO | WO2011150955 | 12/2011 |
| WO | WO2011163582 | 12/2011 |
| WO | WO2012002252 | 1/2012 |
| WO | WO2012014436 | 2/2012 |
| WO | WO2012042908 | 4/2012 |
| WO | WO2012043077 | 4/2012 |
| WO | WO2012043078 | 4/2012 |
| WO | WO2012052172 | 4/2012 |
| WO | WO2012043082 | 5/2012 |
| WO | WO2012067216 | 5/2012 |
| WO | WO2012073499 | 6/2012 |
| WO | WO2012074466 | 6/2012 |
| WO | WO201291016 | 7/2012 |
| WO | WO2012090508 | 7/2012 |
| WO | WO2012101934 | 8/2012 |
| WO | WO2012102034 | 8/2012 |
| WO | WO 2012117764 | 9/2012 |
| WO | WO2012117824 | 9/2012 |
| WO | WO2012132460 | 10/2012 |
| WO | WO 2012/177400 | 12/2012 |
| WO | WO2012170778 | 12/2012 |
| WO | WO2012170779 | 12/2012 |
| WO | WO2012170781 | 12/2012 |
| WO | WO2012170808 | 12/2012 |
| WO | WO2012174026 | 12/2012 |
| WO | WO2013001788 | 1/2013 |
| WO | WO2013046701 | 4/2013 |
| WO | WO2013060733 | 5/2013 |
| WO | WO2014073636 | 5/2014 |
| WO | WO2014078247 | 5/2014 |

* cited by examiner

ABSORBENT ARTICLES WITH CHANNELS AND SIGNALS

FIELD OF THE INVENTION

The present invention relates to absorbent articles with channeled cores and printed signals.

BACKGROUND OF THE INVENTION

Absorbent articles for receiving and retaining bodily discharges such as urine or feces are well known in the art. Examples of these include disposable diapers, training pants and adult incontinence articles. Typically, disposable diapers comprise a liquid pervious topsheet that faces the wearer's body, a liquid impervious backsheet that faces the wearer's clothing and an absorbent core interposed between the liquid pervious topsheet and the backsheet.

An important component of disposable absorbent articles is the absorbent core/absorbent structure. The absorbent core/structure typically includes superabsorbent polymer material, such as hydrogel-forming polymer material, also referred to as absorbent gelling material, AGM, or superabsorbent polymer, SAP. This superabsorbent polymer material ensures that large amounts of bodily fluids, e.g. urine, can be absorbed by the absorbent article during its use and be locked away, thus providing low rewet and good skin dryness.

Traditionally, the superabsorbent polymer material is incorporated into the absorbent core structure with pulp, i.e. cellulose fibers. To make the absorbent core structures thinner, it has been proposed to reduce or eliminate these cellulose fibers from the absorbent core structures.

However, it was found that some absorbent core structures with reduced cellulose fiber levels, while very thin when not loaded with bodily fluids, may have an increased stiffness when partially loaded or fully loaded, especially in those regions which comprise most of the absorbent capacity of the absorbent article, such as the front region and crotch region of the diaper. It has been found that by providing specific permanent channels that are free of superabsorbent polymer particles or free of superabsorbent polymer material, improved liquid transport is achieved, and hence faster acquisition, and more efficient liquid absorbency over the whole absorbent structure; even though less absorbent material may be used, improved performance can be achieved. By immobilizing the absorbent material or channels, by the use of adhesive, the channels are more permanent, and remain channels during the use of the absorbent structure, e.g. when friction is applied to the absorbent structure, or when the absorbent structure is wetted, and the absorbent material expands. Furthermore, it has been found that by the provision of such channels, for example in the front region of the absorbent core/structure, and/or in the crotch region of the absorbent core/structure, a diaper of increased flexibility can be provided, while maintaining its performance throughout its use.

As the functionality of the absorbent core is changed to improve, e.g. absorbency, fit, or reduced cost, the process capability and/or performance and/or appearance of the article may be affected negatively. Efforts can be made to modify the article or parts of the article in order to provide them with a particular appearance. In some examples, the article may be modified to communicate or signal to the caregiver that the channels exist in the absorbent core of the article, and that the channels are there to create faster and more efficient liquid absorbency. Such signalling or communication may be done, for example, via exterior graphics and/or interior printed adhesives.

Due to the intersection of process capability, technical product performance, and successful consumer communication it is important to understand the interaction of these three components to design the right balanced product design. While running the process in a way that best meets consumer communication it can cause negative impacts to the technical performance of the product. While running the best consumer communication design and the right technical product design could result in a process that is not capable of ongoing production. An optimized process and product design combination may not deliver the optimum in consumer communication. As such, there is a need for improved absorbent articles comprising absorbent cores with channels that exhibit excellent process capability, technical product performance, and have a successful consumer communication.

SUMMARY OF THE INVENTION

The present invention is directed to an absorbent article comprising a topsheet, a backsheet, an absorbent core comprising channels disposed between the topsheet and the backsheet, and a printed adhesive layer disposed between the topsheet and the absorbent core such that the printed adhesive layer is visible through the topsheet. At least a portion of the adhesive layer forms a pattern of one or more pairs of contoured lines that run lengthwise in the machine direction of the absorbent article, each pair being symmetric to its compliment across an axis of the absorbent article drawn in the machine direction and at the center of its width. The distance between the innermost pair of contoured lines is from about 15 mm to about 25 mm or the amount of adhesive comprising the printed adhesive layer is such that the pattern coverage with the adhesive is from about 15% to about 30%.

DETAILED DESCRIPTION OF THE INVENTION

Definitions

Figure 1:
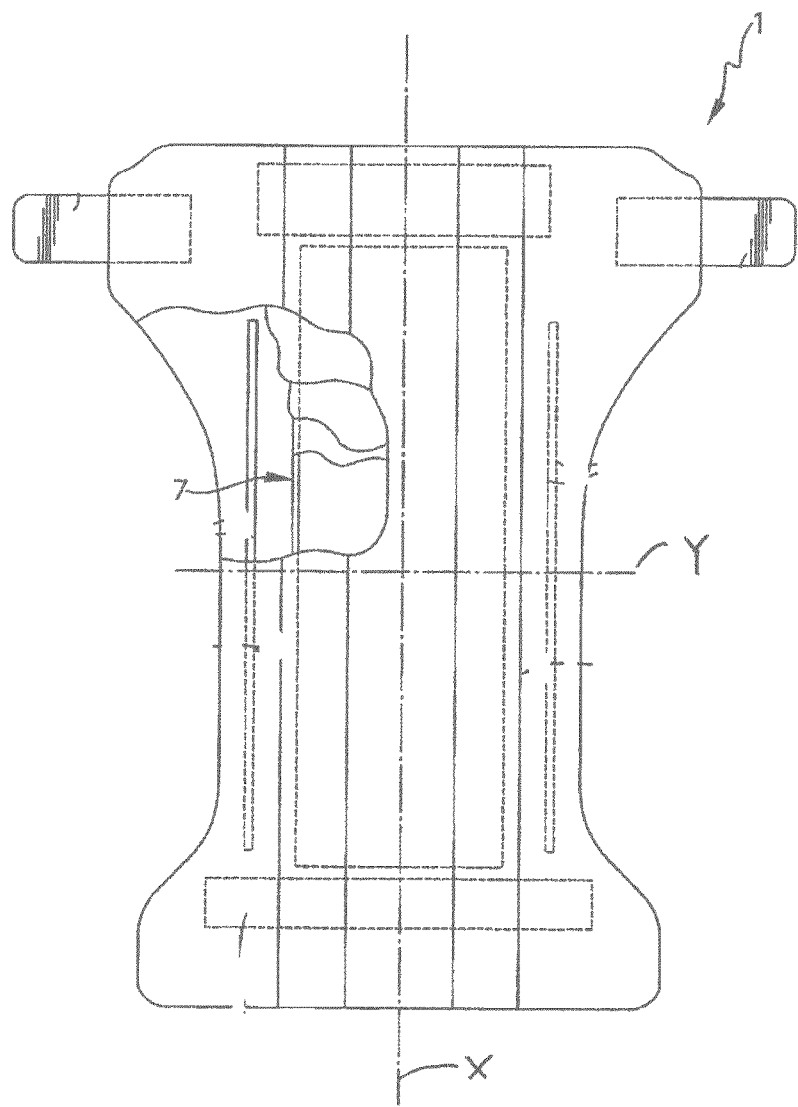
FIG. 1 shows a plan view of a diaper in accordance with one non-limiting embodiment.

"Absorbent article" refers to a device that absorbs and contains body exudates, and, more specifically, refers to devices that are placed against or in proximity to the body of the wearer to absorb and contain the various exudates discharged from the body. Absorbent articles may include adult and infant diaper, including pants, such as infant training pants and adult incontinence undergarments, and feminine hygiene products, such as sanitary napkins and panty-liners and adult in continent pads, and breast pads, care mats, bibs, wound dressing products, and the like. Absorbent articles may further include floor cleaning articles, food industry articles, and the like. As used herein, the term "body fluids" or "body exudates" includes, but is not limited to, urine, blood, vaginal discharges, breast milk, sweat and fecal matter.

As used herein "diaper" refers to devices which are intended to be placed against the skin of a wearer to absorb and contain the various exudates discharged from the body. Diapers are generally worn by infants and incontinent persons about the lower torso so as to encircle the waist and legs of the wearer. Examples of diapers include infant or adult diapers and pant-like diapers such as training pants. "Training pant", as used herein, refers to disposable garments having a waist opening and leg openings designed for infant or adult wearers. A pant may be placed in position on the wearer by inserting the wearer's legs into the leg openings and sliding the pant into position about a wearer's lower torso. A pant may be pre-formed by any suitable technique including, but not limited to, joining together portions of the article using refastenable and/or non-refastenable bonds (e.g., seam, weld, adhesive, cohesive bond, fastener, etc.). A pant may be pre-formed anywhere along the circumference of the article (e.g., side fastened, front waist fastened).

"Disposable" is used herein to describe articles that are generally not intended to be laundered or otherwise restored or reused (i.e., they are intended to be discarded after a single use and, may be recycled, composted or otherwise disposed of in an environmentally compatible manner). As used herein "absorbent structure" refers to a three dimensional structure useful to absorb and contain liquids, such as urine. The absorbent structure may be the absorbent structure of an absorbent article or may be only part of the absorbent core of an absorbent article, i.e. an absorbent component of the absorbent core, as will be further described herein.

"Superabsorbent polymer material" as used herein refers to substantially water-insoluble polymer material that can absorb at least 10 times (and typically at least 15 times or at least 20 times) its weight of a 0.9% saline solution in de-mineralized water as measured using the Centrifuge Retention Capacity test (Edana 441.2-01).

"Nonwoven material" as used herein refers to a manufactured web of directionally or randomly orientated fibers, excluding paper and products which are woven, knitted, tufted, stitch-bonded incorporating binding yarns or filaments, or felted by wet-milling, whether or not additionally needled. Nonwoven materials and processes for making them are known in the art. Generally, processes for making nonwoven materials comprise laying fibers onto a forming surface, which may comprise spunlaying, meltblowing, carding, airlaying, wetlaying, coform and combinations thereof. The fibers may be of natural or man-made origin and may be staple fibers or continuous filaments or be formed in situ.

"Visible" as used herein means capable of being perceived by the unaided human eye.

The present invention provides absorbent articles with absorbent cores comprising channels and printed signals that communicate the channels, such as those disclosed in U.S. Ser. No. 14/077,355 filed on 12 Nov. 2013. Further, the present invention provides absorbent articles with absorbent cores comprising channels and printed signals that communicate the channels. The present invention relates to absorbent articles with channels disclosed in U.S. application Ser. Nos. 13/491,642, 13/491,643, 13/491,644, and 13/491,648, all filed Jun. 10, 2011.

The absorbent structure (13) herein comprises a supporting sheet (16) with an absorbent layer (17) of absorbent material (50). The absorbent material (50) comprises at least a superabsorbent polymer material and optionally a cellulosic material, such as a cellulose, e.g. pulp, or modified cellulose.

The absorbent structure (13) also comprises one or more adhesive materials, further described below. The absorbent layer (17) is three dimensional and comprises a first substantially longitudinal channel (26) and a second substantially longitudinal channel (26) that are substantially free of said superabsorbent polymer material. Other materials may be present in said channels (26), as further described below, for example said one or more adhesive materials (40; 60).

The absorbent structure (13) and the absorbent layer (17) each have a longitudinal dimension and average length L, e.g. extending in the longitudinal dimension of the structure or layer and a transverse dimension and average width W, e.g. extending in the transverse dimension of the structure or layer. The absorbent structure (13) and the absorbent layer (17) each have a front region, being in use towards the front of the user, back region, being in use towards the back of the user, and therein between a crotch region, each extending the full transverse width of the structure/layer, and each having 1/3 of the average length of the structure/layer.

The absorbent structure (13) and the absorbent layer (17) each possess a central longitudinal axis X, a central transverse axis Y perpendicular to said central longitudinal axis X; said absorbent layer (17) and said absorbent structure (13) have each a pair of opposing longitudinal side edges extending in the longitudinal dimension of the structure or layer and a pair of opposing transverse edges (19), e.g. front transverse edge being in use towards the front of a user (wearer), and a back transverse edge being in use towards the back of a user. The longitudinal side edges (18) and/or transverse edges (19) of the absorbent structure (13) or absorbent layer (17) may be parallel respectively to the central longitudinal axis and/or central transverse axis respectively or one or more may be curvilinear, and for instance provide for a narrower transverse dimension in the crotch region. Typically the longitudinal side edges are mirror images of one another in the longitudinal X-axis.

The central longitudinal X-axis of the absorbent layer (17) delimits first and second longitudinal side portions (20) of the absorbent layer (17), respectively, referred herein as longitudinal side portions (20). Each of said longitudinal side portions is thus present in said front region, crotch region and back region, and hence, there is a first longitudinal portion's front region, and a second longitudinal portion's front region etc. In some embodiments herein, said longitudinal portions of the absorbent layer (17) are mirror images of one another in the X-axis of the layer.

The absorbent layer (17) comprises at least a first channel (26) and second channel (26) that are substantially free of (e.g. free of) said superabsorbent polymer particles, said channels (26) extending through the thickness (height) of the absorbent layer (17). It should be understood that, accidentally, a small, negligible amount of superabsorbent polymer particles may be present in the channel, which does not contribute to the overall functionality. When the absorbent layer (17) comprises cellulosic or cellulose, in some embodiments the said first and second channels (26) are also free of such cellulosic/cellulose material.

The first channel (26) is present in said first longitudinal side portion of the absorbent layer (17) and the second channel (26) is present in said second longitudinal side portion of the absorbent layer (17).

The first and second channel (26) each extend substantially longitudinally, which means typically that each channel (26) extends more in the longitudinal dimension than in the transverse dimension, and typically at least twice as much in the longitudinal dimension than in the transverse dimension.

Thus, this includes channels (26) that are completely longitudinal and parallel to the longitudinal direction of said absorbent layer (17) (i.e. paralleled to said longitudinal-axis); and this includes channels (26) that may be curved, provided the radius of curvature is typically at least equal (optionally at least 1.5 or at least 2.0 times this average transverse dimension) to the average transverse dimension of the absorbent layer; and this includes channels (26) that are straight but under an angle of (e.g. from 5°) up to 30°, or for example up to 20°, or up to 10° with a line parallel to the longitudinal axis. This may also include channels with an angle therein, provided said angle between two parts of a channel is at least 120°, at least 150°; and in any of these cases, provided the longitudinal extension of the channel is more than the transverse extension.

In some embodiments, there may be no completely or substantially transverse channels present in at least said crotch region, or no such channels at all.

Each of said first and second channels (26) may have an average width W' that is least 4% of the average width W of said absorbent layer (17), or for example W' is at least 7% of W; and/or for example and up to 25% of W, or up to 15% of W; and/or for example at least 5 mm; and for example up to 25 mm, or for example up to 15 mm.

Each of said first and second channels (26) may have an average length L' which may for example be up to 80% of the average length L of said absorbent layer (17); if the channels (26) are only in the front region, or only in the crotch region, or only in the back region, L' is for example up to 25% of L, or up to 20% of L, and/or L' is for example at least 5% of L, or at least 10% of L; and/or L' is for example at least 10 mm, or at least 20 mm; if the channels (26) extend in said crotch region and front region, and optionally the back region, L' is for example up to 80% of L, or up to 70% of L, and/or L' is for example at least 40% of L, at least 50% of L. In case the channel is not parallel to the longitudinal axis, the length L' of the channel is the length as measured by projection against the longitudinal axis.

The channels (26) may typically be so-called "permanent" channels (26). By permanent, it is meant that the integrity of the channels (26) is at least partially maintained both in the dry state and in the wet state, including during friction by the wearer thereon. Permanent channels (26) may be obtained by provision of one or more adhesive material that immobilize said absorbent material (50), and/or said channels (26), e.g. or said absorbent layer (17), and/or that immobilize said supporting sheet (16) into said channels (26), or part thereof. The absorbent cores (7) may comprise in particular permanent channels formed by bonding of the first supporting sheet (16) and second supporting sheet (16') through the channels. Typically, glue may be used to bond both supporting sheets throught the channel, but it is possible to bond via other known means, for example ultrasonic bonding, or heat bonding. The supporting layers can be continuously bonded or intermittently bonded along the channels.

Indeed, the inventors observed that such channels provide for fast liquid acquisition which reduces risk of leakages. The permanent channels help to avoid saturation of the absorbent layer in the region of fluid discharge (such saturation increases the risk of leakages). Furthermore, in contrast to what would be expected, while decreasing the overall amount of superabsorbent polymer material in the absorbent structure is reduced (by providing channels free of such material), the fluid handling properties of the absorbent structure, or diaper, are improved. Permanent channels, also have the further advantages that in wet state the absorbent material cannot move within the core and remains in its intended position, thus providing better fit and fluid absorption.

Figure 3:
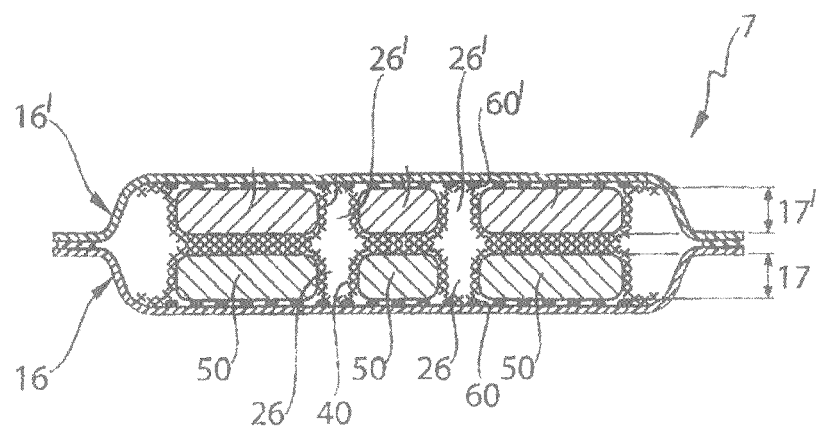
FIG. 3 shows a cross sectional view of an absorbent core in accordance with one non-limiting embodiment.

As for example shown in FIG. 3, one or more adhesive materials (60) may be present between said supporting sheet (16) and said absorbent layer (17), or parts thereof (e.g. herein referred to as, "second adhesive material"). For example, an adhesive material is applied to portions of said supporting sheet (16) that are to coincide with the channels (26), so that in said channels the supporting sheet can be bonded with said adhesive to the walls of the channel, or part thereof or to a further material, as described herein; and/or the adhesive may be applied to portions of the supporting sheet (16) that are to coincide with the absorbent material (50), to immobilize said material and avoid extensive migration thereof into said channels; the adhesive may be applied over substantially the whole surface area of the supporting sheet (16), e.g. substantially continuously and/or homogeneously. This may for example be a hotmelt adhesive applied by printing, slot coating or spraying.

In addition, or alternatively, the absorbent structure (13) may comprise one or more adhesive materials (40) applied on said absorbent layer (17) or part thereof, that is already supported by said supporting sheet (16), (herein referred to as "first adhesive material") e.g. after said absorbent material (50) is combined with/deposited on said supporting sheet (16) to form an absorbent layer (17). This may for example be a thermoplastic fibrous adhesive, as described herein after. It some embodiments, this may be applied continuously over the absorbent layer (17), hence over the absorbent material (50) and in the channels (26), to immobilize the absorbent layer and to optionally also adhere the supporting sheet in said channel, as described above. This is for example shown in FIG. 3.

It should be understood that the first and second adhesive material may be the same type of adhesive, for example as a thermoplastic hotmelt adhesive, for example as described below, the difference between the first and second adhesive thus being the location where it is applied.

In some embodiments, said one or more adhesive material are at least present in the channels (26), for example at least said first adhesive material, or both said first and second adhesive material. It may thus be present on the longitudinal walls of the channels (26) (extending the height of the absorbent layer (17) and the length thereof). If the supporting sheet (16) material folds into said channels (26), or part thereof, e.g. the supporting sheet (16) has undulations into said channels (26) or part thereof, said undulations may be fixed to said walls or part thereof, to ensure the channels (26) are maintained (at least partially) during use.

The first and second channels (26) may be mirror images of one another with respect to the central longitudinal axis (X-axis) of the absorbent layer (17)/structure.

In some embodiments, there is no channel (26) that coincides with said longitudinal axis of said absorbent layer (17). The channels (26) may be spaced apart from one another over their whole longitudinal dimension. The smallest spacing distance D (the distance between the innermost pair of the contoured lines) may for example be at least 5% of average transverse dimension W of layer, or for example at least 10% of W, or at least 15% of W.

Furthermore, in order to reduce the risk of fluid leakages, the longitudinal main channels (26) typically do not extend up to any of the transverse edges (19) and/or longitudinal edges (18) of the absorbent layer (17). Typically, the smallest distance I' between a channel (26) and the nearest longitudinal edge corresponds to at least 5% of W, or for example to at least 10% of W. In some embodiments, the distance is for example at least 10 mm; the smallest distance between a channel and the nearest transverse edge (19) of the absorbent layer (17) may for example be at least 5% of the average length L of the layer.

Figure 2:
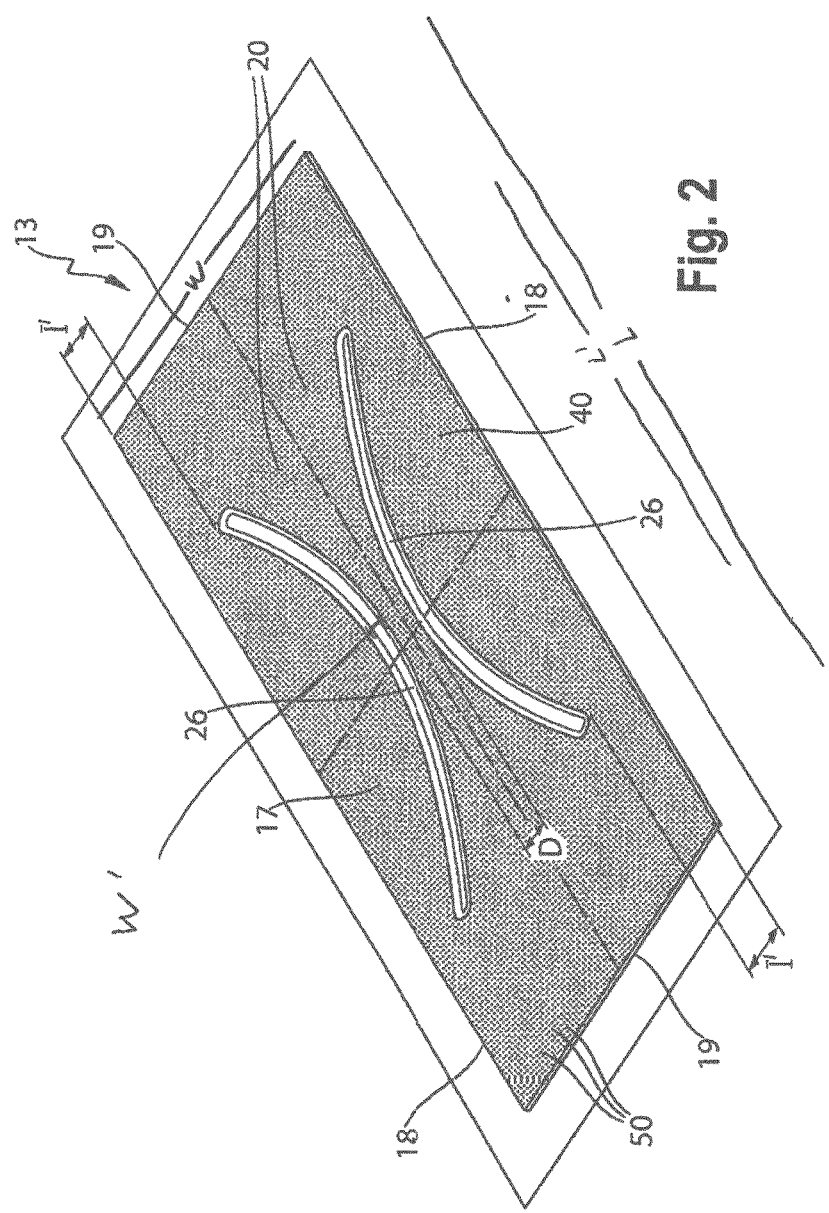
FIG. 2 shows a perspective view of an absorbent structure in accordance with one non-limiting embodiment.

The absorbent structure may comprise only two channels, for example only in the front region, or for example in the central (crotch) region, and optionally extending into the front and/or back region, such as shown FIG. 2.

The absorbent structure (13) may comprise more than two of such channels (26), for example at least 4, or at least 5 or at least 6. Some or all of these may be substantially parallel to one another, for example being all straight and completely longitudinally, and/or two or more or all may be mirror images of one another in the longitudinal axis, or two or more may be curved or angled and fore example mirror images of one another in the longitudinal axis, and two or more may be differently curved or straight, and for example mirror images of one another in the longitudinal axis.

For example the front region of the absorbent layer (17) may comprise two or more channels (26), that are typically mirror images of one another in the longitudinal axis of the layer, and the crotch region may comprise two or more channels (26), that are typically mirror images of one another in the longitudinal axis of the layer, and the latter may optionally extend into the front region and/or back region, with any of applicable dimensions and other characteristics described above. Optionally, further channels may be present in the back region.

The first and second channels (26), and optionally further channels (26), may be positioned in said absorbent layer (17) such that there is a central longitudinal strip, coinciding with said longitudinal axis, which is free of any channels (26); said absorbent material (50) may be substantially continuously present in said strip. For example, said strip may have a minimum width D (the distance between the innermost pair of the contoured lines) of at least 5% of W, or at least 10% of W.

In some embodiments, in said central longitudinal strip between two neighboring channels (26) the average basis weight of absorbent material (50), or of said superabsorbent polymer material, is at least 350, and for example up to 1000 grams per m$^2$, or for example from 450 grams per m$^2$, and for example up to 750 grams per m$^2$.

In some embodiments, adjacent each first and second channel, and optionally adjacent said further channels, said absorbent material (50) is substantially continuously present.

The absorbent structure (13) typically comprises one or more further materials (e.g. a further material layer) to cover the absorbent layer (17), herein referred to as further material; the further material may be a layer comprising adhesive, for example on the surface that is to contact the absorbent layer (17) of the absorbent structure (13) herein. Thus, the further material may comprise, on the surface to be placed adjacent said absorbent layer (17) of the absorbent structure (13), an adhesive material.

The resulting structure is herein referred to as "absorbent core (7)". An example thereof is shown in FIG. 3.

This further material may be a further absorbent structure, with a second absorbent layer (17') and a second supporting sheet (16'), so that both absorbent layers (17, 17') are sandwiched between said supporting sheets (16; 16'); this may be a further absorbent structure of the disclosure, with two or more channels (26') as described herein, and for example shown in FIG. 3; or this may be an absorbent structure as described herein but without channels; and/or it may be an absorbent structure as described herein but without adhesive.

The second absorbent structure may be identical to the first absorbent structure (13), or they may both be absorbent structure with channels (26; 26') of the disclosure, but they may be different, for example having different channels, different number of channels, different adhesive, different adhesive application or combinations thereof.

The channels (26), or some of those, of the first absorbent structure (13) and the channels (26') of the second absorbent structure, or some of those, may coincide and overlap with one another; e.g. completely or for example coincide only partially and overlap only partially; or some or all of the channels (26; 26') may even not coincide and not overlap one another. In some embodiments they are about identical to one another and the channels (26) of one structure substantially completely coincide and overlap the channels (26) of another structure.

In some embodiments, the further material may be a part of the supporting sheet (16), which is folded over the absorbent layer (17) and then sealed along the peripheral edges, to enclose the absorbent layer (17).

In some embodiments, the further material is a further supporting sheet (16'), i.e. the absorbent structure (13) is covered with a further supporting sheet (16'), said absorbent layer then being sandwiched between the two supporting sheets.

In some embodiments, the further material may be an acquisition material layer and/or an acquisition sheet, for example sealed to said supporting sheet (16). In some embodiments, the further material includes a further absorbent structure, e.g. any of those described above, or further supporting sheet (16'), and then combined with an acquisition material layer, and optionally a further acquisition sheet.

The further material may also be an acquisition material layer present adjacent said absorbent layer (17), the acquisition material layer optionally comprising chemically cross-linked cellulosic fibers, and the acquisition material layer being supported on a second supporting sheet (16'). The absorbent layer (17) and the acquisition material layer may then be sandwiched between said supporting sheet (16) of the first structure and said second supporting sheet (16'). The acquisition material layer may also further comprise channels (26'), in particular substantially completely overlapping with the channels (26) of said first absorbent structure (13).

The supporting sheet (16) of the first structure and/or the second supporting sheet (16') of the acquisition material layer may fold into the channels (26) of the first absorbent structure (13) and/or optionally into the channels (26') of the acquisition material layer, if present, or part of these channels (26, 26'). The one or more adhesive materials may be at least present in the channels (26, 26'), or part thereof, and the supporting sheets (16, 16') may be adhered to one another in said channels (26, 26') by one or more of these adhesive materials. Another second adhesive (60') may be present between the second supporting sheet (16') and the acquisition material layer. Another adhesive may be placed between the acquisition material layer and the absorbent layer (17), in addition to the thermoplastic adhesive (40), to improve better adhesion of both layers.

In any of these cases, the further material can then be sealed to the supporting sheet (16) along the peripheral edges thereof, to enclose the absorbent layers (17; optionally 17').

In any of these cases the supporting sheet (16) or acquisition layer/sheet may fold into (i.e. undulate into) said channels (26) or part thereof. It may be adhered to the supporting sheet (16) of the absorbent structure (13) of the disclosure in said channels (26), e.g. by an adhesive material, as described herein. Alternatively, or in addition, it may be adhered to the walls of the channels (26 and/or 26') or part thereof.

In some embodiments the absorbent structure (13) comprises such a further material overlaying said absorbent layer (17), and a pressure means is applied selectively to said supporting sheet (16) and/or to said further material, in those parts that coincide with said channels (26 and/or 26'), to pressurize said supporting sheet (16) and/or said further material into said channels of the absorbent structure (13) and/or into the channels of a further (second) absorbent structure if present (into channels 26 and/or 26', if present), to aid formulation of said undulations and/or to aid adhering of the further material and said supporting sheet (16) to one another in said channels (26 and/or 26'), if an adhesive material is present as described herein.

The pressure means may be a pressure roll with raised portions that have substantially the size, shape, pattern of said channels (26 and/or 26'), that can coincide (i.e.: mate) with said parts of the supporting sheet (16) or further material coinciding with said channels (26 and/or 26').

In some embodiments, the further (e.g. second) supporting sheet (16') may be wider than the absorbent structure to enable the second supporting sheet (16') to fold into the channels (26 and/or 26') or part thereof, and thereby may adhere to the first supporting sheet (16).

In embodiments wherein the absorbent core (7) comprises two (or more) absorbent structures comprising the channels (26; 26'), described herein, it may be that one or two, or more, or all, of the channels (26) of one absorbent structure (13) substantially superpose the channels (26') of the adjacent absorbent structure. The resulting absorbent core (7) is then a laminate of absorbent structures with channels (26; 26'), wherein the channels (26; 26') extend substantially through the thickness of the absorbent layers (17;17').

In addition or alternatively, it may be that one or two, or more, or all, channels (26) of one absorbent structure (13) do not superpose the channels (26') of the adjacent absorbent structure; they may for example be complementary with the channels (26) of the adjacent structure. By complementary it is meant that the channels (26') of the second absorbent structure form an extension of the channels (26) of the first absorbent structure (13).

In some embodiments, the absorbent core (7) may comprise two or more absorbent structures (13), one of which being the structure of the disclosure, and one being an absorbent structure (13) with a supporting sheet (16') with thereon an absorbent layer (17') (with superabsorbent polymer material) without channels and/or without adhesive.

If a second absorbent structure is present in the absorbent core (7), this may comprise one or more adhesives, in the manner as described above, and for the reasons described above.

For example, it may be present such that it coincides with the channels (26) of the first absorbent structure (13) at least, and/or with its channels (26'), if present.

The absorbent layer (17) comprises absorbent material (50) that comprises superabsorbent polymer material (e.g. particles), optionally combined with cellulosic material (including for example cellulose, comminuted wood pulp in the form of fibers). The further material described above (e.g. a further, second absorbent structure may include an absorbent material, and the following may apply thereto too).

In some embodiment, the absorbent material (50) may comprise at least 60%, or at least 70% by weight of superabsorbent polymer material, and at the most 40% or at the most 30% of cellulosic material.

In some other embodiments, the absorbent layer (17) comprises absorbent material (50) that consists substantially of absorbent polymer material, e.g. particles, e.g. less than 5% by weight (of the absorbent material (50)) of cellulosic material is present; and said absorbent layer (17)/absorbent structure (13), may be free of cellulosic material.

Typically, the superabsorbent polymer material is in the form of particles. Suitable for use in the absorbent layer (17) can comprise any superabsorbent polymer particles known from superabsorbent literature, for example such as described in Modern Superabsorbent Polymer Technology, F. L. Buchholz, A. T. Graham, Wiley 1998. The absorbent polymer particles may be spherical, spherical-like or irregular shaped particles, such as Vienna-sausage shaped particles, or ellipsoid shaped particles of the kind typically obtained from inverse phase suspension polymerizations. The particles can also be optionally agglomerated at least to some extent to form larger irregular particles.

In some embodiments herein, the absorbent material (50) as a whole and/or said particulate superabsorbent polymer material at least, has a high sorption capacity, e.g. having a CRC of for example at least 20 g/g, or at 30 g/g. Upper limits may for example be up to 150 g/g, or up to 100 g/g.

In some embodiments herein, the absorbent material (50) comprising or consisting of superabsorbent polymer particles that are formed from polyacrylic acid polymers/polyacrylate polymers, for example having a neutralization degree of from 60% to 90%, or about 75%, having for example sodium counter ions.

The superabsorbent polymer may be polyacrylates and polyacrylic acid polymers that are internally and/or surface cross-linked. Suitable materials are described in the PCT Patent Application WO 07/047598 or for example WO 07/046052 or for example WO2009/155265 and WO2009/155264. In some embodiments, suitable superabsorbent polymer particles may be obtained by current state of the art production processes as is more particularly described in WO 2006/083584. The superabsorbent polymers may be internally cross-linked, i.e. the polymerization is carried out in the presence of compounds having two or more polymerizable groups which can be free-radically copolymerized into the polymer network. Useful crosslinkers include for example ethylene glycol dimethacrylate, diethylene glycol diacrylate, allyl methacrylate, trimethylolpropane triacrylate, triallylamine, tetraallyloxyethane as described in EP-A 530 438, di- and triacrylates as described in EP-A 547 847, EP-A 559 476, EP-A 632 068, WO 93/21237, WO 03/104299, WO 03/104300, WO 03/104301 and in DE-A 103 31 450, mixed acrylates which, as well as acrylate groups, include further ethylenically unsaturated groups, as described in DE-A 103 31 456 and DE-A 103 55 401, or crosslinker mixtures as described for example in DE-A 195 43 368, DE-A 196 46 484, WO 90/15830 and WO 02/32962 as well as cross-linkers described in WO2009/155265. The superabsorbent polymer particles may be externally surface cross-linked, or post cross-linked. Useful post-crosslinkers include compounds including two or more groups capable of forming covalent bonds with the carboxylate groups of the polymers. Useful compounds include for example alkoxysilyl compounds, polyaziridines, polyamines, polyamidoamines, di- or polyglycidyl compounds as described in EP-A 083 022, EP-A 543 303 and EP-A 937 736, polyhydric alcohols as described in DE-C 33 14 019, cyclic carbonates as described in DE-A 40 20 780, 2-oxazolidone and its derivatives, such as N-(2-hydroxyethyl)-2-oxazolidone as described in DE-A 198 07 502, bis- and poly-2-oxazolidones as described in DE-A 198 07 992, 2-oxotetrahydro-1,3-oxazine and its derivatives as described in DE-A 198 54 573, N-acyl-2-oxazolidones as described in DE-A 198 54 574, cyclic ureas as described in DE-A 102 04 937, bicyclic amide acetals as described in DE-A 103 34 584, oxetane and cyclic ureas as described in EP-A 1 199 327 and morpholine-2,3-dione and its derivatives as described in WO 03/031482.

The superabsorbent polymers or particles thereof may have surface modifications, such as being coated or partially coated with a coating agent. Examples of coated absorbent polymer particles are disclosed in WO2009/155265. The coating agent may be such that it renders the absorbent polymer particles more hydrophilic. For example, it may be hydrophilic (i.e. fumed) silica, such as Aerosils. The coating agent may be a polymer, such as an elastic polymer or a film-forming polymer or an elastic film-forming polymer, which forms an elastomeric (elastic) film coating on the particle. The coating may be a homogeneous and/or uniform coating on the surface of the absorbent polymer particles. The coating agent may be applied at a level of from 0.1% to 5%.

The superabsorbent polymer particles may have a particle sizes in the range from 45 μm to 4000 μm, more specifically a particle size distribution within the range of from 45 μm to about 2000 μm, or from about 100 μm to about 1000 or to 850 μm. The particle size distribution of a material in particulate form can be determined as it is known in the art, for example by means of dry sieve analysis (EDANA 420.02 "Particle Size distribution).

In some embodiments herein, the superabsorbent material is in the form of particles with a mass medium particle size up to 2 mm, or between 50 microns and 2 mm or to 1 mm, or from 100 or 200 or 300 or 400 or 500 μm, or to 1000 or to 800 or to 700 μm; as can for example be measured by the method set out in for example EP-A-0691133. In some embodiments of the disclosure, the superabsorbent polymer material is in the form of particles whereof at least 80% by weight are particles of a size between 50 μm and 1200 μm and having a mass median particle size between any of the range combinations above. In addition, or in another embodiment of the disclosure, said particles are essentially spherical. In yet another or additional embodiment of the disclosure the superabsorbent polymer material has a relatively narrow range of particle sizes, e.g. with the majority (e.g. at least 80%, at least 90% or even at least 95% by weight) of particles having a particle size between 50 μm and 1000 μm, between 100 μm and 800 μm, between 200 μm and 600 μm.

The absorbent structure (13) herein comprises a supporting sheet (16) on which said absorbent material (50) is supported and immobilized. The further material may be or include a supporting sheet (16'), and the following applies also to such a sheet (16').

This supporting sheet (16) may be an individual sheet or a web material that is subsequently divided into individual absorbent structures (13), in particular paper, films, wovens or nonwovens, or laminate of any of these.

In some embodiments herein, the supporting sheet (16) is a nonwoven, e.g. a nonwoven web, such as a carded nonwoven, spunbond nonwoven or meltblown nonwoven, and including nonwoven laminates of any of these.

The fibers may be of natural or man-made origin and may be staple or continuous filaments or be formed in situ. Commercially available fibers have diameters ranging typically from less than about 0.001 mm to more than about 0.2 mm and they come in several different forms: short fibers (known as staple, or chopped), continuous single fibers (filaments or monofilaments), untwisted bundles of continuous filaments (tow), and twisted bundles of continuous filaments (yarn). The fibers may be bicomponent fibers, for example having a sheath-core arrangement, e.g. with different polymers forming the sheath and the core. Nonwoven fabrics can be formed by many processes such as meltblowing, spunbonding, solvent spinning, electrospinning, and carding. The basis weight of nonwoven fabrics is usually expressed in grams per square meter (gsm).

The nonwoven herein may be made of hydrophilic fibers; "Hydrophilic" describes fibers or surfaces of fibers, which are wettable by aqueous fluids (e.g. aqueous body fluids) deposited on these fibers. Hydrophilicity and wettability are typically defined in terms of contact angle and the strike through time of the fluids, for example through a nonwoven fabric. This is discussed in detail in the American Chemical Society publication entitled "Contact angle, wettability and adhesion", edited by Robert F. Gould (Copyright 1964). A fiber or surface of a fiber is said to be wetted by a fluid (i.e. hydrophilic) when either the contact angle between the fluid and the fiber, or its surface, is less than 90°, or when the fluid tends to spread spontaneously across the surface of the fiber, both conditions are normally co-existing. Conversely, a fiber or surface of the fiber is considered to be hydrophobic if the contact angle is greater than 90° and the fluid does not spread spontaneously across the surface of the fiber.

The supporting sheet (16) herein may be air-permeable. Films useful herein may therefore comprise micro pores. Nonwovens herein may for example be air permeable. The supporting sheet (16) may have for example an air-permeability of from 40 or from 50, to 300 or to 200 $m^3/(m^2 \times min)$, as determined by EDANA method 140-1-99 (125 Pa, 38.3 $cm^2$). The supporting sheet (16) may alternatively have a lower air-permeability, e.g. being non-air-permeable, to for example be better detained on a moving surface comprising vacuum.

In some executions, the supporting sheet (16) is a nonwoven laminate material, a nonwoven laminate web, for example of the SMS or SMMS type.

In order to form easily said undulations, the supporting sheet (16) may have a basis weight that is less than 60 gsm, or for example than 50 gsm, for example from 5 gsm to 40 gsm, or to 30 gsm.

The supporting sheet (16) may have a CD-extensibility or a MD-extensibility.

In one of the embodiment herein, the supporting sheet (16) has undulations that fold (undulate) into said first and second channels (26), and optionally in to said further channels, of part thereof. For example the undulations may extend over about the full longitudinal dimension of the channel; they may for example extend to complete average height of the absorbent layer (17)/channel, or for example only up to 75% thereof, or up to 50% of the average height of the absorbent layer (17)/channel. This aids immobilization of the absorbent material (50) adjacent said channels (26) and said channels (26) of said layers.

The undulations may be adhered with said one or more adhesive material, e.g. said second adhesive material, to said walls of said channels (26). The supporting sheet (16) may alternatively, or in addition, be adhered in said channels (26) to said further material, e.g. second supporting sheet (16), describe herein above, e.g. with said first and/or second adhesive.

The absorbent structure (13) may comprise one or more adhesive materials. In some embodiments, it comprises a first adhesive material and/or a second adhesive material, as described above, and in the manner described above.

The absorbent core herein may comprise a further second absorbent structure that may comprise one or more adhesive materials; the following equally applies thereto.

Any suitable adhesive can be used for this, for example so-called hotmelt adhesives used. For example, a sprayable hot melt adhesives, such as H.B. Fuller Co. (St. Paul, Minn.) Product No. HL-1620-B, can be used.

The adhesive materials may not only help in immobilizing the absorbent material on the supporting sheet but it may also help in maintaining the integrity of the channels in the absorbent structure absorbent core during storage and/or during use of the disposable article. The adhesive material may help to avoid that a significant amount of absorbent material migrates into the channels. Furthermore, when the adhesive material is applied in the channels or on the supporting sheet portions coinciding with the channels it may thereby help to adhere the supporting sheet of the absorbent structure to said walls, and/or to a further material, as will be described in further details below.

In some embodiments, the first adhesive (40) and/or the second adhesive (60) may be a thermoplastic adhesive material.

In some embodiments, the first adhesive (40) may be applied as fibers, forming a fibrous network that immobilizes the absorbent material on the supporting sheet. The thermoplastic adhesive fibers may be partially in contact with the supporting sheet of the absorbent structure; if applied also in the channels, it (further) anchors the absorbent layer to the supporting sheet.

The thermoplastic adhesive material may for example allow for such swelling, without breaking and without imparting too many compressive forces, which would restrain the absorbent polymer particles from swelling. Thermoplastic adhesive materials (40; 60) suitable for use in the present disclosure includes hot melt adhesives comprising at least a thermoplastic polymer in combination with a plasticizer and other thermoplastic diluents such as tackifying resins and additives such as antioxidants. Exemplary suitable hot melt adhesive materials (40; 60) are described in EP 1447067 A2. In some embodiments, the thermoplastic polymer has a molecular weight (Mw) of more than 10,000 and a glass transition temperature (Tg) below room temperature or $-6°$ C.$>$Tg$<$16° C. In certain embodiments, the concentrations of the polymer in a hot melt are in the range of about 20 to about 40% by weight. In certain embodiments, thermoplastic polymers may be water insensitive. Exemplary polymers are (styrenic) block copolymers including A-B-A triblock structures, A-B diblock structures and (A-B)n radial block copolymer structures wherein the A blocks are non-elastomeric polymer blocks, typically comprising polystyrene, and the B blocks are unsaturated conjugated diene or (partly) hydrogenated versions of such. The B block is typically isoprene, butadiene, ethylene/butylene (hydrogenated butadiene), ethylene/propylene (hydrogenated isoprene), and mixtures thereof.

Other suitable thermoplastic polymers that may be employed are metallocene polyolefins, which are ethylene polymers prepared using single-site or metallocene catalysts. Therein, at least one comonomer can be polymerized with ethylene to make a copolymer, terpolymer or higher order polymer. Also applicable are amorphous polyolefins or amorphous polyalphaolefins (APAO) which are homopolymers, copolymers or terpolymers of C2 to C8 alpha olefins.

The thermoplastic adhesive material, typically a hot-melt adhesive material, is generally present in the form of fibers, i.e. the hot melt adhesive can be fiberized. In some embodiments, the thermoplastic adhesive material forms a fibrous network over the absorbent polymer particles. Typically, the fibers can have an average thickness from about 1 μm to about 100 μm, or from about 25 μm to about 75 μm, and an average length from about 5 mm to about 50 cm. In particular the layer of hot melt adhesive material can be provided such as to comprise a net-like structure. In certain embodiments the thermoplastic adhesive material is applied at an amount of from 0.5 to 30 $g/m^2$, or from 1 to 15 $g/m^2$, or from 1 and 10 $g/m^2$ or even from 1.5 and 5 $g/m^2$ per supporting sheet (16).

A typical parameter for an adhesive suitable for use in the present disclosure can be a loss angle tan Delta at 60° C. of below the value of 1, or below the value of 0.5. The loss angle tan Delta at 60° C. is correlated with the liquid character of an adhesive at elevated ambient temperatures. The lower tan Delta, the more an adhesive behaves like a solid rather than a liquid, i.e. the lower its tendency to flow or to migrate and the lower the tendency of an adhesive superstructure as described herein to deteriorate or even to collapse over time. This value is hence particularly important if the absorbent article is used in a hot climate.

It may be beneficial, e.g. for process reasons and/or performance reasons, that the thermoplastic adhesive material has a viscosity of between 800 and 4000 mPa·s, or from 1000 mPa·s or 1200 mPa·s or from 1600 mPa·s to 3200 mPa·s or to 3000 mPa·s or to 2800 mPa·s or to 2500 mPa·s, at 175° C., as measurable by ASTM D3236-88, using spindle 27, 20 pmp, 20 minutes preheating at the temperature, and stirring for 10 min.

The thermoplastic adhesive material may have a softening point of between 60° C. and 150° C., or between 75° C. and 135° C., or between 90° C. and 130° C., or between 100° C. and 115° C., as can be determined with ASTM E28-99 (Herzog method; using glycerine).

In one embodiment herein, the thermoplastic adhesive component may be hydrophilic, having a contact angle of less than 90°, or less than 80° or less than 75° or less than 70°, as measurable with ASTM D 5725-99.

The absorbent articles of the present invention may comprise signals that communicate to the consumer the functionality and benefits of the absorbent core channels. Non-limiting examples of such signals may include printed adhesive layers, backsheet graphics, embossing of the topsheet and/or acquisition layer, and combinations thereof.

One type of signal that may be used to communicate the existence and the benefits of the channels is a printed adhesive layer. In some embodiments, an article with channels in the core may have a layer of an adhesive that is applied in a pattern that connotes the absorbency and other benefits of the channels. This adhesive layer may be applied to a substrate, such as a supporting layer, in some embodiments an acquisition layer, that may be positioned between a topsheet and the absorbent core with channels. In some embodiments, the layer of printed adhesive may be visible through the topsheet.

In some embodiments, a fluid, such as an adhesive, may be applied or printed onto an advancing substrate. The fluid application apparatus may include a slot die applicator and a substrate carrier. The slot die applicator may include a slot opening, a first lip, and a second lip, the slot opening located between the first lip and the second lip. And the substrate carrier may include one or more pattern elements and may be adapted to advance the substrate past the slot die applicator as the slot die applicator discharges adhesive onto the substrate. In operation, when the first surface of the substrate is disposed on the substrate carrier, the substrate carrier advances the second surface of the substrate past the slot opening of the slot die applicator. In turn, the substrate is intermittently compressed between the slot die applicator and the pattern surface of the pattern element. As the substrate is intermittently compressed, adhesive discharged from the slot die applicator is applied onto the second surface of the advancing substrate in an area having a shape that is substantially the same as a shape defined by the pattern surface. In some embodiments, the adhesive may be a different color than the substrate. The adhesive may comprise pigments or dyes. Other methods and apparatuses involved for the application of adhesives in pre-determined patterns to an advancing substrate are disclosed in U.S. Pat. No. 8,186,296. In some embodiments, the fluid printed on the substrate may be an ink without an adhesive.

The term "pattern" as used herein means a decorative or distinctive design, not necessarily repeating or imitative, including but not limited to the following: marbled, check, mottled, veined, clustered, geometric, spotted, helical, swirl, arrayed, variegated, textured, spiral, cycle, contoured, laced, tessellated, starburst, lobed, lightning, blocks, textured, pleated, cupped, concave, convex, braided, tapered, and combinations thereof. The curves lines of the printed adhesive layer may signal to the consumer one or more benefits of the channels. For example, the channels may act as a conduit, distributing fluid to a more comfortable place, while the printed adhesive layer, visible to the caregiver through the topsheet, may signal or communicate the fluid distribution and comfort that the article can provide.

As discussed above, the absorbent structure of the present invention typically comprises one or more further materials, such as a further material layer, to cover the absorbent layer. This layer may comprise an adhesive, for example on the surface that is to contact the absorbent layer of the absorbent structure. Thus, the further material may comprise on the surface to be placed adjacent said absorbent layer of the absorbent structure, an adhesive material. In some embodiments, the further material layer may be an acquisition material layer that may have the adhesive printed onto it to form a patterned appearance. Thus, the adhesive is printed onto the surface of the acquisition layer that is adjacent to the absorbent core. In addition to an absorbent core with channels and a printed adhesive layer printed onto the surface of the acquisition layer adjacent to the absorbent core, the article may also comprise a topsheet, wherein the printed adhesive layer is visible through the topsheet. In some embodiments, the printing (ink or an adhesive with ink) may be on the topsheet itself, and where ink is the substance being printed, the printing may be performed using digital printing.

In some embodiments, the absorbent article may comprise graphics printed onto the backsheet. As the absorbent core is loaded with fluid, the absorbent material will expand in particular towards the backsheet, while the channels which do not comprise absorbent material will not expand. This difference may be used, as the channels will become more perceptible through the backsheet as fluid is absorbed as they may form depressions. These depressions will become more pronounced as the absorbent article absorbs the fluid.

The depth of these depressions formed by the channels on the backsheet side will be proportional to the amount of fluid absorbed, and the inventors have found that that the visual appearance to the caregiver may be improved by providing a backsheet printing which matches or at least indicates the region of the channels to the caregiver. Thus the backsheet printing may comprise a line or a curve which substantially matches the shape and/or position of the channels.

Backsheet graphics may similarly signal to the caregiver the attributes of the channels. In some embodiments, the only visual signal of the channels may be the backsheet printing. In some embodiments, the backsheet printing may be curves, lines, or other patterns that approximate the shape and contours of the channels. In some embodiments, the article may comprise both a printed adhesive layer and backsheet graphics, the combination of which work together or separately to accentuate certain channel aspects.

The relative lengths of any of the lines above may be expressed as ratios, and may be exact, or may be expressed with a tolerance of plus or minus 2%, 3%, 4%, 5%, 7%, 10%, 12%, 15%, 17%, 20%, 22%, 25%, 27%, 30%, alone or in combination with other ratios of lengths, and the length may be rounded to the nearest whole number or multiple of 5, after the percent of tolerance is applied.

Further, in some embodiments, the graphics visually signaling the inner channels will not extend beyond the area of the outer channels themselves, and/or the area where the absorbent core is present, and in some embodiments, the graphics visually signaling the outer channels will not extend beyond the area of the outer channels themselves, and/or the area where the absorbent core is present, and in some embodiments, the graphics visually signaling the inner and outer channels will not extend beyond the area of the inner and outer channels themselves, and/or the area where the absorbent core is present.

In addition, the article may comprise other or additional visual cues that signal the absorbent core channels, such as, for example, embossing. Embossing may be done on the topsheet or on the absorbent core, or, in some embodiments, there may be multi-layer embossing of both the topsheet and the absorbent core. For example, thermal embossing may be done over the channels (where there is no superabsorbent polymer) at a small gap setting to enhance the visual presence. Any embossing may be done alone or in combination with printing to help signal the absorbent core channels. Further, any embossing may be done to the topsheet, core, or both, on-line (during assembly of the absorbent article's component parts) or prior to such assembly, e.g. at the site where a supplier of component parts makes the component part itself.

In some embodiments, the printed adhesive layer or the backsheet printing may be a pattern that covers the majority or even all of the absorbent core. In other embodiments, the printed adhesive layer or backsheet printing may be printed only in discrete areas. For example, in some embodiments, the printed adhesive layer or backsheet printing may be printed so as to not overlap or intersect with the absorbent core channels. The term "overlap" as used herein means to cover over a part of, or to have an area in common. The term "intersect" as used herein means items that cut across or through each other, or that narrow and merge.

In order to ensure that absorbent article components (including graphic absorbent article components) are properly oriented when attached to other absorbent article components, registration may be used. Registration may include using a system to detect a location on an absorbent article component and to compare the location against a set point (which may be an operator desired or machine set location). The system may adjust placement of the absorbent article component in accordance with said comparison. For example, the location of absorbent core channels and a printed adhesive layer may be detected and a repeat length of the printed adhesive layer may be altered via a length control system (described in U.S. Pat. Nos. 6,444,064 and 6,955,733). Alternatively, a system may be used to detect and control the longitudinal or machine direction position of a component relative to a desired position on the absorbent article wherein the position at which subsequent occurrences of a first component is attached to a second component is altered to ensure the first component is in the desired location. Such can be performed based on multiple detections and the use of an averaging position, deviation from the desired position, or by detecting less frequently than every occurrence. Additionally, a system may detect a first location on a first absorbent article component and a second location on a second absorbent article component, where the first and second locations may be compared relative to each other and against a set point or desired offset position. The system may adjust placement of the first and/or second absorbent article components in accordance with said comparison. Combinations of detection methods may be used.

In some embodiments, registration may be used to optimize the visual impression of the printing and the absorbent core channels.

In some embodiments, any printing, whether a printed adhesive layer, a backsheet graphic, or some combination, may match, or substantially match the shape or contour of the absorbent core channels. In some embodiments, the printing will not necessarily match or overlap or correlate with the shape or contour of the absorbent core channels, but will otherwise communicate or signal to the consumer the existence and/or benefits of the channels.

The absorbent structure (13) or absorbent core (7) herein may be useful in an absorbent article, such as described above, and in particular in a diaper (1), including fastenable diapers (1) and (refastenable) training pants, for infants or for adults, or in an absorbent pad, such as a sanitary napkin or adult incontinence undergarment pad.

The article may comprise, in addition to an absorbent structure (13) or absorbent core (7) as described herein, a topsheet and backsheet, and for example one or more side flaps or cuffs. The topsheet or cuffs or side flaps may comprise a skin care composition or lotion or powder, known in the art, panels, including those described in U.S. Pat. Nos. 5,607,760; 5,609,587; 5,635,191; 5,643,588.

Articles herein comprise a topsheet, facing the wearer in use, for example a nonwoven sheet, and/or an apertured sheet, including apertured formed films, as known in the art, and a backsheet.

The backsheet may be liquid impervious, as known in the art. In some embodiments, the liquid impervious backsheet comprises a thin plastic film such as a thermoplastic film having a thickness of about 0.01 mm to about 0.05 mm. Suitable backsheet materials comprise typically breathable material, which permit vapors to escape from the diaper (1) while still preventing exudates from passing through the backsheet. Suitable backsheet films include those manufactured by Tredegar Industries Inc. of Terre Haute, Ind. and sold under the trade names X15306, X10962 and X10964.

The backsheet, or any portion thereof, may be elastically extendable in one or more directions. The backsheet may be attached or joined to a topsheet, the absorbent structure/core, or any other element of the diaper (1) by any attachment means known in the art.

Diapers herein may comprise leg cuffs and/or barrier cuffs; the article then typically has a pair of opposing side flaps and/or leg and/or barrier cuffs, each of a pair being positioned adjacent one longitudinal side of the absorbent structure/core, and extending longitudinally along said structure/core, and typically being mirror images of one another in the longitudinal-axis of the article; if leg cuffs and barrier cuffs are present, then each leg cuffs is typically positioned outwardly from a barrier cuff. The cuffs may be extending longitudinally along at least 70% of the length of the article. The cuffs may have a free longitudinal edge that can be positioned out of the X-Y plane (longitudinal/transverse directions) of the article, i.e. in z-direction. The side flaps or cuffs of a pair may be mirror images of one another in the longitudinal axis of the article. The cuffs may comprise elastic material.

The diapers herein may comprise a waistband, or for example a front waistband and back waist band, which may comprise elastic material.

The diaper (1) may comprise side panels, or so-called ear panels. The diaper (1) may comprise fastening means, to fasten the front and back, e.g. the front and back waistband. Fastening systems may comprise fastening tabs and landing zones, wherein the fastening tabs are attached or joined to the back region of the diaper (1) and the landing zones are part of the front region of the diaper (1).

The absorbent structure (13) may be combined with, and the absorbent core (7) or diaper (1) may comprise, an acquisition layer and/or acquisition material layer, or system thereof this may comprise chemically cross-linked cellulosic fibers. Such cross-linked cellulosic fibers may have desirable absorbency properties. Exemplary chemically cross-linked cellulosic fibers are disclosed in U.S. Pat. No. 5,137,537. In certain embodiments, the chemically cross-linked cellulosic fibers are cross-linked with between about 0.5 mole % and about 10.0 mole % of a $C_2$ to $C_9$ polycarboxylic cross-linking agent or between about 1.5 mole % and about 6.0 mole % of a $C_2$ to $C_9$ polycarboxylic cross-linking agent based on glucose unit. Citric acid is an exemplary cross-linking agent. In other embodiments, polyacrylic acids may be used. Further, according to certain embodiments, the cross-linked cellulosic fibers have a water retention value of about 25 to about 60, or about 28 to about 50, or about 30 to about 45. A method for determining water retention value is disclosed in U.S. Pat. No. 5,137,537. According to certain embodiments, the cross-linked cellulosic fibers may be crimped, twisted, or curled, or a combination thereof including crimped, twisted, and curled.

In a certain embodiment, one or both of the upper and lower acquisition layers may comprise a non-woven, which may be hydrophilic. Further, according to a certain embodiment, one or both of the upper and lower acquisition layers may comprise the chemically cross-linked cellulosic fibers, which may or may not form part of a nonwoven material. According to an exemplary embodiment, the upper acquisition layer may comprise a nonwoven, without the cross-linked cellulosic fibers, and the lower acquisition layer may comprise the chemically cross-linked cellulosic fibers. Further, according to an embodiment, the lower acquisition layer may comprise the chemically cross-linked cellulosic fibers mixed with other fibers such as natural or synthetic polymeric fibers. According to exemplary embodiments, such other natural or synthetic polymeric fibers may include high surface area fibers, thermoplastic binding fibers, polyethylene fibers, polypropylene fibers, PET fibers, rayon fibers, lyocell fibers, and mixtures thereof. Suitable nonwoven materials for the upper and lower acquisition layers include, but are not limited to SMS material, comprising a spunbonded, a melt-blown and a further spunbonded layer. In certain embodiments, permanently hydrophilic non-wovens, and in particular, nonwovens with durably hydrophilic coatings are desirable. Another suitable embodiment comprises a SMMS-structure. In certain embodiments, the nonwovens are porous.

The diaper (1) may include a sub-layer disposed between the topsheet and the absorbent structure (13)/absorbent core (7), capable of accepting, and distributing and/or immobilizing bodily exudates. Suitable sublayers include acquisition layers, surge layers and or fecal material storage layers, as known in the art. Suitable materials for use as the sub-layer may include large cell open foams, macro-porous compression resistant nonwoven highlofts, large size particulate forms of open and closed cell foams (macro and/or microporous), highloft non-wovens, polyolefin, polystyrene, polyurethane foams or particles, structures comprising a multiplicity of vertically oriented, looped, strands of fibers, or apertured formed films, as described above with respect to the genital coversheet. (As used herein, the term "microporous" refers to materials that are capable of transporting fluids by capillary action, but having a mean pore size of more than 50 microns. The term "macroporous" refers to materials having pores too large to effect capillary transport of fluid, generally having pores greater than about 0.5 mm (mean) in diameter and more specifically, having pores greater than about 1.0 mm (mean) in diameter, but typically less than 10 mm or even less than 6 mm (mean).

Processes for assembling the absorbent article or diaper (1) include conventional techniques known in the art for constructing and configuring disposable absorbent articles. For example, the backsheet and/or the topsheet can be joined to the absorbent structure/core or to each other by a uniform continuous layer of adhesive, a patterned layer of adhesive, or an array of separate lines, spirals, or spots of adhesive. Adhesives which have been found to be satisfactory are manufactured by H. B. Fuller Company of St. Paul, Minn. under the designation HL-1258 or H-2031. While the topsheet, the backsheet, and the absorbent structure (13)/core may be assembled in a variety of well-known configurations, diaper (1) configurations are described generally in U.S. Pat. No. 5,554,145 entitled "Absorbent Article With Multiple Zone Structural Elastic-Like Film Web Extensible Waist Feature" issued to Roe et al. on Sep. 10, 1996; U.S. Pat. No. 5,569,234 entitled "Disposable Pull-On Pant" issued to Buell et al. on Oct. 29, 1996; and U.S. Pat. No. 6,004,306 entitled "Absorbent Article With Multi-Directional Extensible Side Panels" issued to Robles et al. on Dec. 21, 1999.

As discussed above, there is a need for providing absorbent articles with absorbent cores that comprise channels and printed signals that communicate the channels. A further need exists in that the particular combinations of channels and printed signals can be optimized to improve such communication.

Figure 4A:
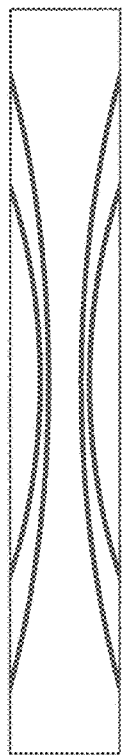
FIGS. 4a and 4b show top view representations of non-limiting embodiments of printed adhesive patterns.
Figure 4B:
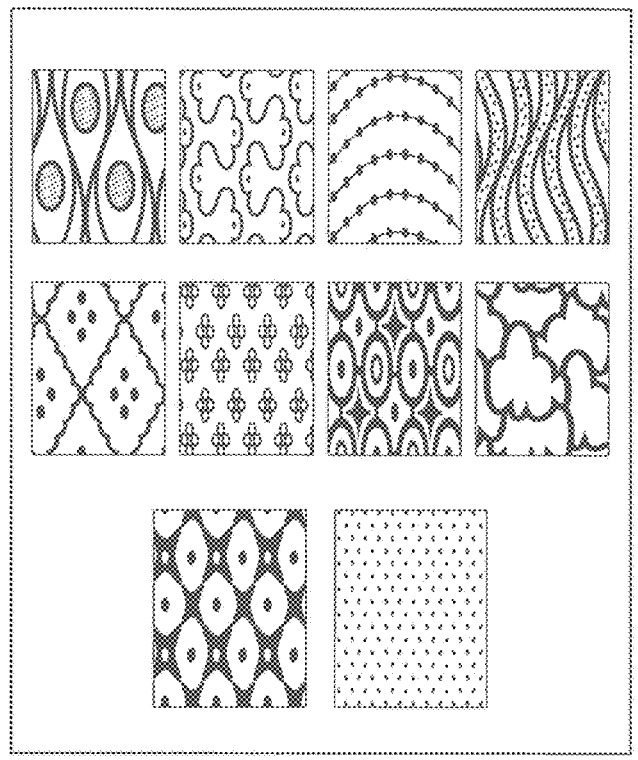

The inventors have contemplated providing signals comprising two elements: an underlay (as shown in FIG. 4a) and a pattern fill (as shown in FIG. 4b). The signals themselves may comprise adhesive, ink, or both, or blends of adhesive and ink.

However, there are difficulties in attempting to find combinations of underlays and pattern fills that would provide sufficient visual appeal to caregivers with the technical and cost feasibilities of mass-producing absorbent articles. The distance between the channels' innermost contoured lines D may be important in providing absorbent cores that exhibit excellent process capability, technical product performance, and have a successful consumer communication. If the distance between the contoured lines D is too small, the process capability may be negatively impacted by equipment wear and material wrapping. Further, product performance may be negatively impacted by slower acquisition speeds. If the distance between the contoured lines D is too large, the process capability may be negatively impacted by not having enough contact to remove adhesive, thereby causing contamination. Further, consumer communication may be negatively impacted by a pattern that is not consistently visible and a low color intensity.

Further, the adhesive coverage area may be important in providing absorbent cores that exhibit excellent process capability, technical product performance, and have a successful consumer communication. If the adhesive coverage area is too small, the process capability may be negatively impacted by not having enough glue coverage to maintain control of the patch in process. Further, consumer communication may be negatively impacted by not having enough adhesive pattern to deliver a consumer message. If the adhesive coverage area is too great, the process capability may be negatively impacted by having too much adhesive to deliver the process consistently. Further, consumer communication may be negatively impacted by leading to a lack of absorbency signaling.

Figure 5A:
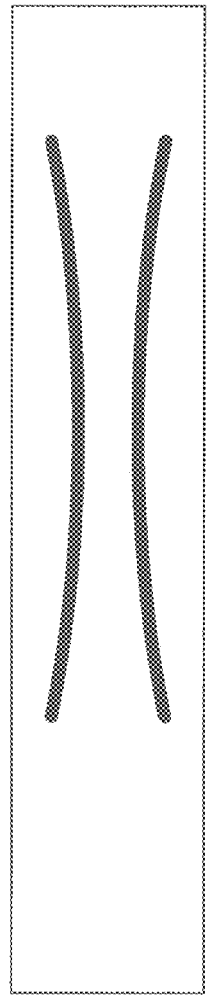
FIGS. 5a and 5b show top view representations of non-limiting embodiments of printed adhesive patterns.
Figure 5B:
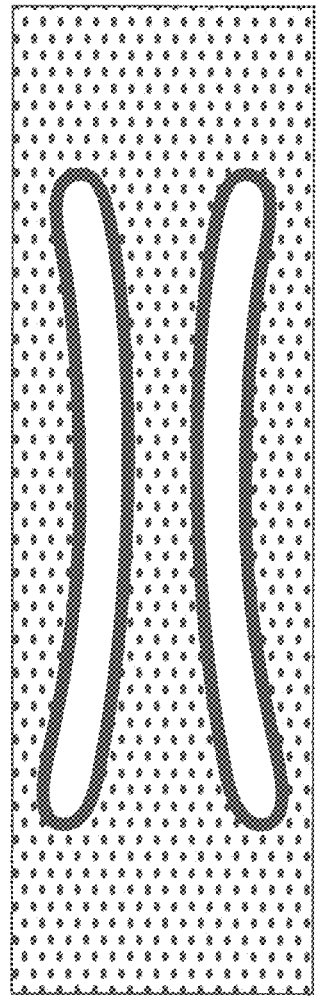

Combinations such as those shown in FIGS. 5a and 5b, are found to be visually successful but technically not feasible. For example, these designs may be perceived as providing too much white space in between the contoured lines, e.g. more than 25 mm, which is difficult to achieve from a manufacturing standpoint. Overall this design may not provide enough adhesive to hold the absorbent article components together, as pattern coverage with the adhesive is less than 15%, and may also be difficult to manufacture due to centerline difficulties.

Figure 6A:
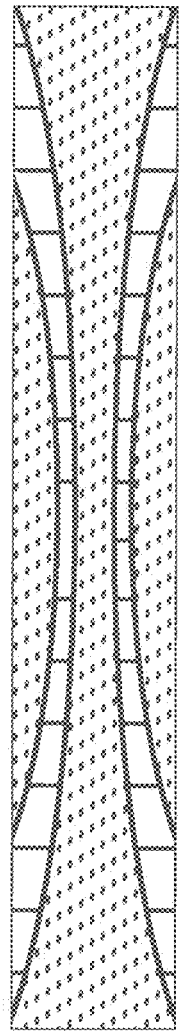
FIGS. 6a and 6b show top view representations of non-limiting embodiments of printed adhesive patterns of the present invention.
Figure 6B:
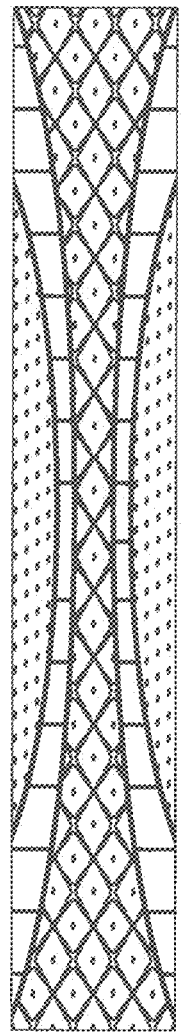

Combinations such as those shown in FIGS. 6a and 6b, are found to be visually successful and technically feasible. For example, these designs may be perceived as balancing the placement and amount of adhesive which allows for sufficient bonding of absorbent article layer components to each other, and also allows for good fluid handling, and process-ability. These designs may be perceived as providing a suitable amount of space in between the contoured lines, e.g. from 15 mm to 25 mm, which is able to be achieved from a manufacturing standpoint. Overall this design may suitably provide enough adhesive to hold the absorbent article components together, as pattern coverage with the adhesive is from 15% to 30%, and may be suitable to manufacture due to centerline being established, e.g. for base conditions to deliver at about 150N of force (nozzle to substrate+plate).

Figure 7A:
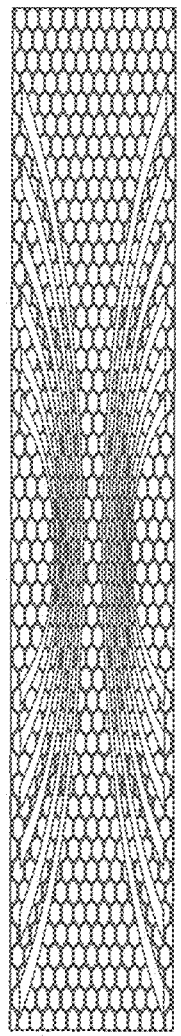
FIGS. 7a and 7b show top view representations of non-limiting embodiments of printed adhesive patterns.
Figure 7B:
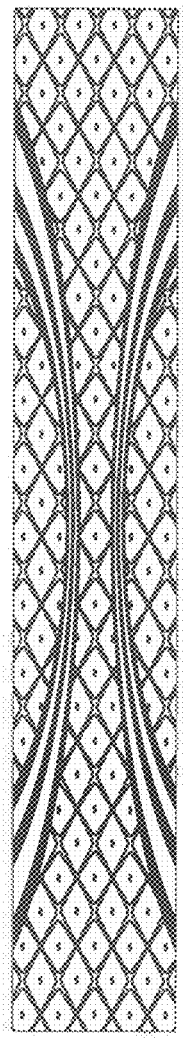

Combinations such as those shown in FIGS. 7a and 7b, are found to be visually unsuccessful and technically not feasible. For example, these designs may be perceived as providing not enough contrast between the underlay and the fill pattern. Overall this design may provide too much adhesive for proper fluid handling, as pattern coverage with the adhesive is more than 30%, and may also be difficult to manufacture due to centerline difficulties.

As such, in some embodiments of the present invention, the distance between the innermost pair of contoured lines is from about 10 mm to about 30 mm, from about 15 mm to about 25 mm, from about 18 mm to about 22 mm, less than about 30 mm, less than about 25 mm, more than about 10 mm, more than about 15 mm.

As such, in some embodiments of the present invention, the amount of adhesive comprising the printed adhesive layer is such that the pattern coverage with the adhesive is from about 10% to about 35%, from about 15% to about 30%, from about 20% to about 25%, less than about 35%, less than about 30%, more than about 10%, more than about 15%.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. An absorbent article comprising:
   a topsheet, a backsheet, an absorbent core disposed between the topsheet and the backsheet, and a printed adhesive layer comprising an adhesive and being disposed between the topsheet and the absorbent core;
   wherein the absorbent core comprises absorbent material and channels, wherein said channels are substantially free of absorbent material;
   wherein the printed adhesive layer is visible through the topsheet and comprises an adhesive pattern coverage of 15% to 30%;
   wherein at least a portion of the adhesive layer forms a pattern of one or more pairs of contoured lines that run lengthwise in the machine direction of the absorbent article, each pair comprising contoured lines that are symmetric and each concave with respect to an axis of the absorbent article drawn in the machine direction and at the center of its width;
   wherein another portion of the printed adhesive layer comprises a printed underlay; and
   wherein an innermost pair of contoured lines is separated by a lateral distance of 15 mm to 25 mm;
   wherein the absorbent core channels are contoured; and wherein the printed adhesive layer substantially matches the contour of the absorbent core channels and
   wherein the absorbent core channels are symmetric and mirror images of one another with respect to the axis of the absorbent article drawn in the machine direction and at the center of its width.

2. The absorbent article of claim 1, further comprising an acquisition layer disposed between the topsheet and the absorbent core, wherein the printed adhesive layer is printed onto the acquisition layer.

3. The absorbent article of claim 2, wherein the printed adhesive layer is a different color than that of the acquisition layer.

4. The absorbent article of claim 3, wherein the acquisition layer has a surface that is adjacent to the absorbent core, and the printed adhesive layer is printed onto the surface of the acquisition layer that is adjacent to the absorbent core.

5. The absorbent article of claim 1, wherein the absorbent article further comprises graphics printed on the backsheet.

6. The absorbent article of claim 5, wherein the graphics printed on the backsheet substantially match the pattern of the printed adhesive layer.

7. The absorbent article of claim 1, wherein the topsheet comprises embossing.

8. The absorbent article of claim 1, wherein the channels and the pattern of the printed adhesive layer do not overlap.

9. An absorbent article comprising:
   a topsheet, a backsheet, an absorbent core disposed between the topsheet and the backsheet, and a printed adhesive layer comprising an adhesive and being disposed between the topsheet and the absorbent core;
   wherein the absorbent core comprises an absorbent layer having absorbent material and channels, wherein the channels are substantially free of absorbent material;
   wherein the printed adhesive layer is visible through the topsheet and comprises an adhesive pattern coverage of 15% to 30%;
   wherein the absorbent layer comprises an average length and is delimited by two transverse edges and two longitudinal edges;
   wherein the absorbent core channels are contoured and do not extend to any of the transverse edges such that each channel is separated from each transverse edge by a minimum distance that is at least 5% of the average length of the absorbent layer; and
   wherein the printed adhesive layer comprises a pattern that substantially matches the contour of the absorbent core channels.

* * * * *